United States Patent
Lee et al.

(10) Patent No.: US 10,385,061 B2
(45) Date of Patent: Aug. 20, 2019

(54) MEDICARPIN, ITS DERIVATIVES, MANUFACTURING METHOD THEREOF

(71) Applicant: PhytoHealth Corporation, Taipei (TW)

(72) Inventors: Kuo-Hsiung Lee, Chapel Hill, NC (US); Rong-Tsun Wu, Taipei (TW); Xiao-Ming Yang, Shanghai (CN); Yu Zhao, Shanghai (CN); Lin-Yea Horng, Taipei (TW); Hui-Ching Sung, Taipei (TW); Pei-Lun Hsu, Taipei (TW); Chien-Hsin Cheng, Taipei (TW); Yi-Li Lee, Taipei (TW)

(73) Assignee: Phytohealth Corporation, Taipei (TW)

(*) Notice: Subject to any disclaimer, the term of this patent is extended or adjusted under 35 U.S.C. 154(b) by 0 days.

(21) Appl. No.: 15/713,183

(22) Filed: Sep. 22, 2017

(65) Prior Publication Data

US 2018/0086772 A1    Mar. 29, 2018

Related U.S. Application Data

(60) Provisional application No. 62/398,832, filed on Sep. 23, 2016.

(51) Int. Cl.
*C07D 493/04*    (2006.01)

(52) U.S. Cl.
CPC .................. *C07D 493/04* (2013.01)

(58) Field of Classification Search
CPC .................................................. C07D 493/04
See application file for complete search history.

(56) References Cited

PUBLICATIONS

Higgins and Smith, Phytopathology, vol. 62, pp. 235-238, Feb. 1972.*
Suginome et al., Experientia (1962), 18, 163-4.*
McGookin et al. J. Chem. Soc., 1940, 0, 787-795.*

* cited by examiner

*Primary Examiner* — Rebecca L Anderson
(74) *Attorney, Agent, or Firm* — Muncy, Geissler, Olds & Lowe, P.C.

(57) ABSTRACT

A compound and use thereof are provided. The compound of the invention has formula I shown below. Each variable in formula I,

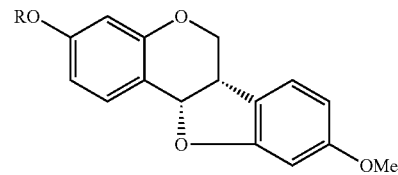

Formula I is defined in the specification. The invention also provides a method for treating renal and cardiac dysfunction. The method includes administering to a subject in need thereof an effective amount of the compound of the invention and a pharmaceutical acceptable salt and carrier.

12 Claims, 28 Drawing Sheets

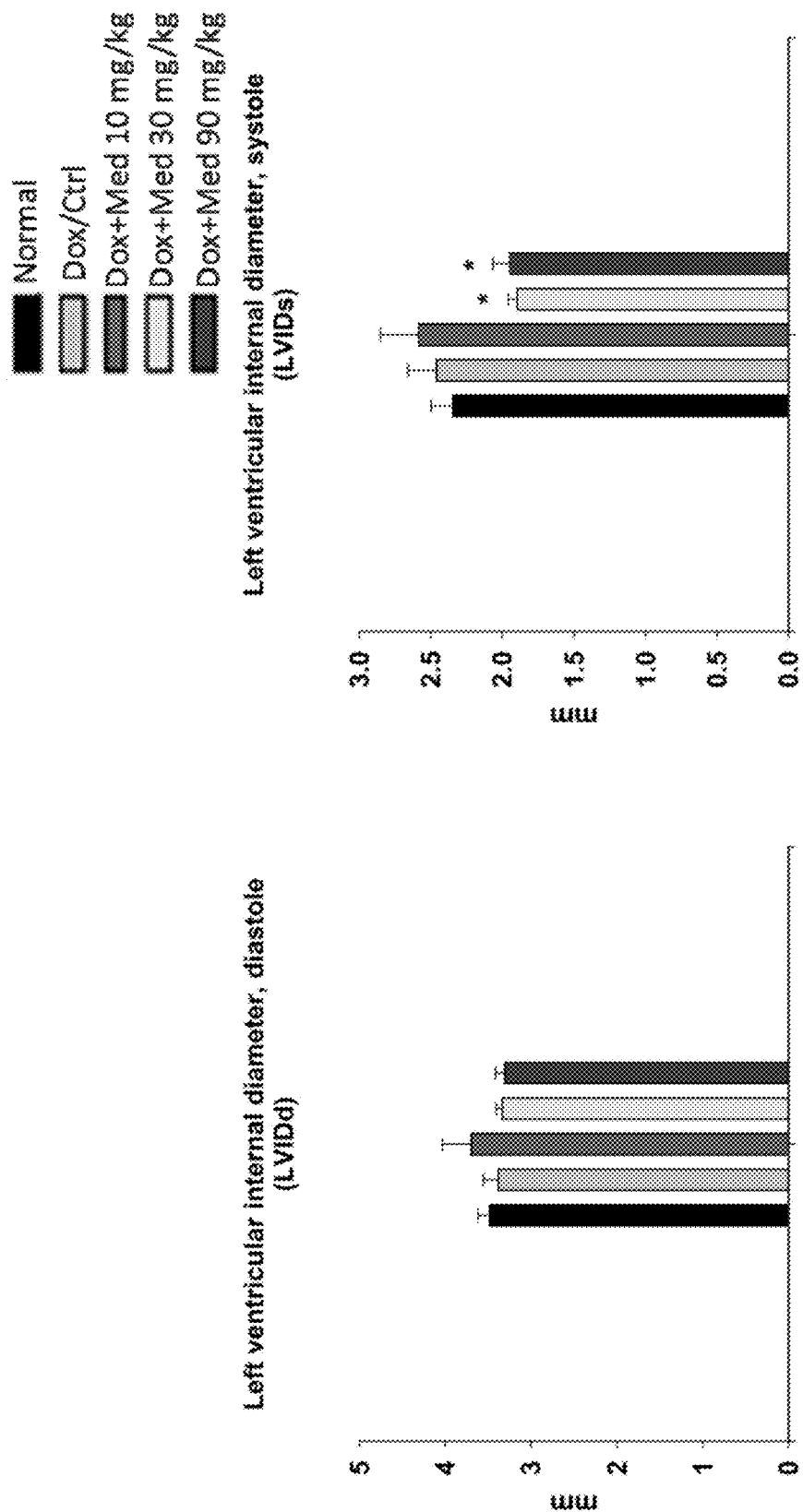

MEDICARPIN, ITS DERIVATIVES, MANUFACTURING METHOD THEREOF

CROSS-REFERENCE TO RELATED APPLICATIONS

This Non-provisional application claims priority under 35 U.S.C. § 119(a) on Patent Application No. 62/398,832 filed in United States America Sep. 23, 2016, the entire contents of which are hereby incorporated by reference.

FIELD OF THE INVENTION

The present invention relates to medicarpin and its derivatives, and its preparation method and also relates to the effect of medicarpin and its derivatives for treating and preventing organ dysfunction.

BACKGROUND OF THE INVENTION

Ischemia causes oxygen deprivation, cell injury and related organ dysfunctions, such as heart failure, stroke, chronic obstructive pulmonary disease, ischemic retinopathy, liver injury and acute renal failure. Mitochondrial dysfunction is a key factor in organ ischemia injury; upon loss of oxygen, mitochondrial oxidative phosphorylation rapidly stops, with a resulting loss of the major source of ATP production for energy metabolism.

Erythropoietin (EPO) is essential for the regulation of the mass of erythrocytes in response to changes in tissue oxygenation during hypoxia and anemia. The protective effects of EPO have been demonstrated in various tissues and experimental models of ischemia-induced injury and have been attributed to its effect on non-haematopoietic metabolic adaptation, inhibition of apoptosis and stimulation of angiogenesis. Recently, EPO has been reported to stimulate cardiac mitochondrial proliferation through the activation of mitochondrial biogenesis, which is mediated by PPAR co-activator 1-α (PGC-1α), a key regulator of cardiac bioenergetics. Clinically, EPO reverses cardiac remodeling, improves cardiac function, and enhances the exercise tolerance and quality of life of patients by inducing protective effects beyond the correction of anaemia (Bergmann et al., 2011). These findings highlight the possibility that EPO-mediated protection may depend on its modulatory effects on intracellular energetic.

Haemoglobin (Hb) is the main oxygen transporter in erythrocytes. Its main form, Hb-α, is a tetramer consisting of two α- and β-polypeptide chains, each carrying a haeme group. Recently, Hb was unexpectedly found to be expressed in many non-haematopoietic cells and it is possible that it facilitates tissue oxygen transport or increases cellular oxygenation and so provides an intrinsic protective mechanism against hypoxic/ischemic injury.

Recombination Human Erythropoietin (rHuEPO) is used for treating chronic heart failure, it can reverse cardiac remodeling, improve heart function, antiapoptotic effects, anti-inflammation, anti-fibrosis and also improving aneamia symptom and sport capacity. However, high dosages of rHuEPO were needed for the treatment, and it caused higher rates of thrombosis and stroke. Darbepoetin alfa was proved to increase the risk of stroke in anemic, heart failure patient and chronic kidney disease patient and not even have a significant treatment efficacy. Moreover, according to the result of REVEAL trail, epoetin alfa did not reduce infarct size and was associated with higher rates of adverse cardiovascular events and increase in infarct size among older patients.

In conclusion, clinical practice should avoid rHuEPO treatment to higher hemoglobin targets, particularly in those with significant cardiovascular morbidity and those who require disproportionately high dosages of rHuEPO to achieve recommended hemoglobin levels. Compare to rHuEPO, small molecular compound can easily go through myocardial tissue to the myocardial cells. Therefore, it is necessary to develop a drug which is a small molecular compound, low-dosage needed and stimulating endogenous EPO.

*Astragalus propinquus* (syn. *Astragalus membranaceus*) is the dried roots of *Astragalus membranaceus* (Fisch.) Bge. Var. Mongholicus (Bge.) Hsiao or *Astragalus membranaceus* (Fisch.) Bge., which are the plants of the family Fabaceae. It is the most widely used herbs in traditional Chinese medicine because it can help diuretic, lower blood pressure and enhance energy.

In previously study, *Astragalus propinquus* is known that rich in polysaccharides, glucuronides, several amino acids, cholines, flavonoids and folates, etc. However, the extractions from *Astragalus propinquus* by present technology are the mixture. Therefore, it is necessary to develop a novel preparation method to obtain a pure and small molecule component of *Astragalus propinquus*.

SUMMARY OF THE INVENTION

In view of the above-mentioned problem, the present invention provides a medicarpin and its derivatives, a method of preparing medicarpin and its derivatives, and a method for enhancing cell activities and improving organ functions using medicarpin and derivatives thereof.

The invention provides a compound as shown in formula I.

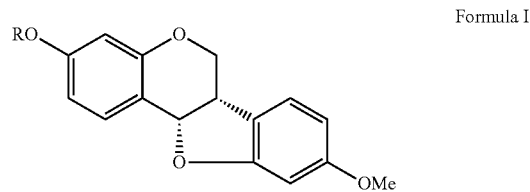

Formula I wherein R is

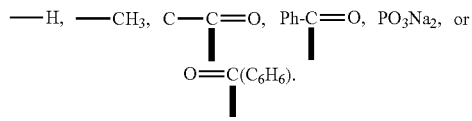

The invention provides a compound, wherein the compound is medicarpin or derivatives thereof.

The invention further provides the compound, wherein the compound including a pharmaceutical acceptable salt and carrier.

The invention also provides a method for preparing the compound of the present invention comprising the steps as shown in FIGS. 1 and 2.

A method for prepare an *Astragalus propinquus* small molecule, comprising: (1) protecting phenols by TBS and Benzyl to give a compound 1 and 2; (2) the compound 2 underwent Wittig reaction to afford a compound 3; (3) hydrolyzing and further oxidizing to give a compound 5; (4) introducing a auxiliary group to give a compound 6; (5) carrying out a coupling reaction to furnish a compound 7; (6) protecting a hydroxyl group with MOMCl; (7) reducing a intermediate with NaBH4 to a compound 9; (8) generating a compound 11 by Intramolecular Mitsunobu reaction; and (9) affording (+)-Medicarpin using CSA (Cam phosulfonic acid) in dichloromethane.

The invention also provides a method for treating organ dysfunction in a subject, wherein the method comprising administrating to said subject a pharmaceutical composition; wherein the pharmaceutical composition comprising the present compound and a pharmaceutical acceptable salt and carrier; wherein the pharmaceutical composition is performed subcutaneously, intravenously, intrathecally, or intramuscularly. The concentration of the compound is 0.1~10 μg. The dose of the pharmaceutical composition is 30-90 mg/kg.

The invention also provides a method for treating organ dysfunction in a subject, wherein the organ comprises a cardiac or a renal; wherein the compound can stimulate the proliferation and differentiation of erythroid progenitor cells and increase the number of red blood cells (RBC), white blood cell (WBC) and platelet (PLT) and ameliorate the cardiac ischaemia.

The invention also provides a method for treating organ dysfunction in a subject, wherein the dysfunction of the renal is an acute renal failure induced by chemotherapy agent. The pharmaceutical composition can increase an oxygen carrying capacity of red blood cells in blood, increase the number of white blood cell (WBC). The pharmaceutical composition can accelerate renal cortex cell regeneration.

The invention also provides a method for treating organ dysfunction in a subject, wherein the dysfunction of the cardiac is a cardiomyopathy induced by chemotherapy agent. The pharmaceutical composition can reduce the cardiomyocytes atrophy, hypertrophy, apoptosis or myocardial fibrosis. In particularly, the cardiomyocytes is ventricular tissue cell, the pharmaceutical composition can increase endurance under normoxic condition.

BRIEF DESCRIPTION OF THE DRAWINGS

FIG. 3A-1, FIG. 3A-2, FIG. 3B are graphs showing the quantification of the differentiated erythroid progenitors from mouse bone marrow. Medicarpin and its derivates enhanced the differentiation of erythroid progenitor cells at low concentration (0.1 to 10 μg/mL), wherein YXM-M3 (derivative compound 3) and YXM-M5 (derivative compound 5) had a higher erythropoietin stimulating activity.

FIGS. 11A-11D are graphs showing the effect of medicarpin on cardiac function in doxorubicin-induced mice by using electrocardiography on week 3. The mice treated with medicarpin (30 and 90 mg/kg) had significantly greater fractional shortening (FIG. 11A) and ejection fractions (FIG. 11B).

DETAILED DESCRIPTION OF THE INVENTION

In one aspect of the invention, the present invention provides a compound as shown in formula I.

Formula I

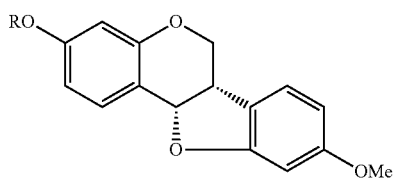

where R is

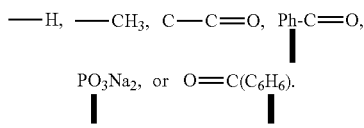

The compound of the present invention is medicarpin or its derivatives.

In one embodiment, the medicarpin or derivatives thereof can be isolated from *Astragalus propinquus* or be synthesized by chemical processes, preferably chemical processes.

Figure 1:
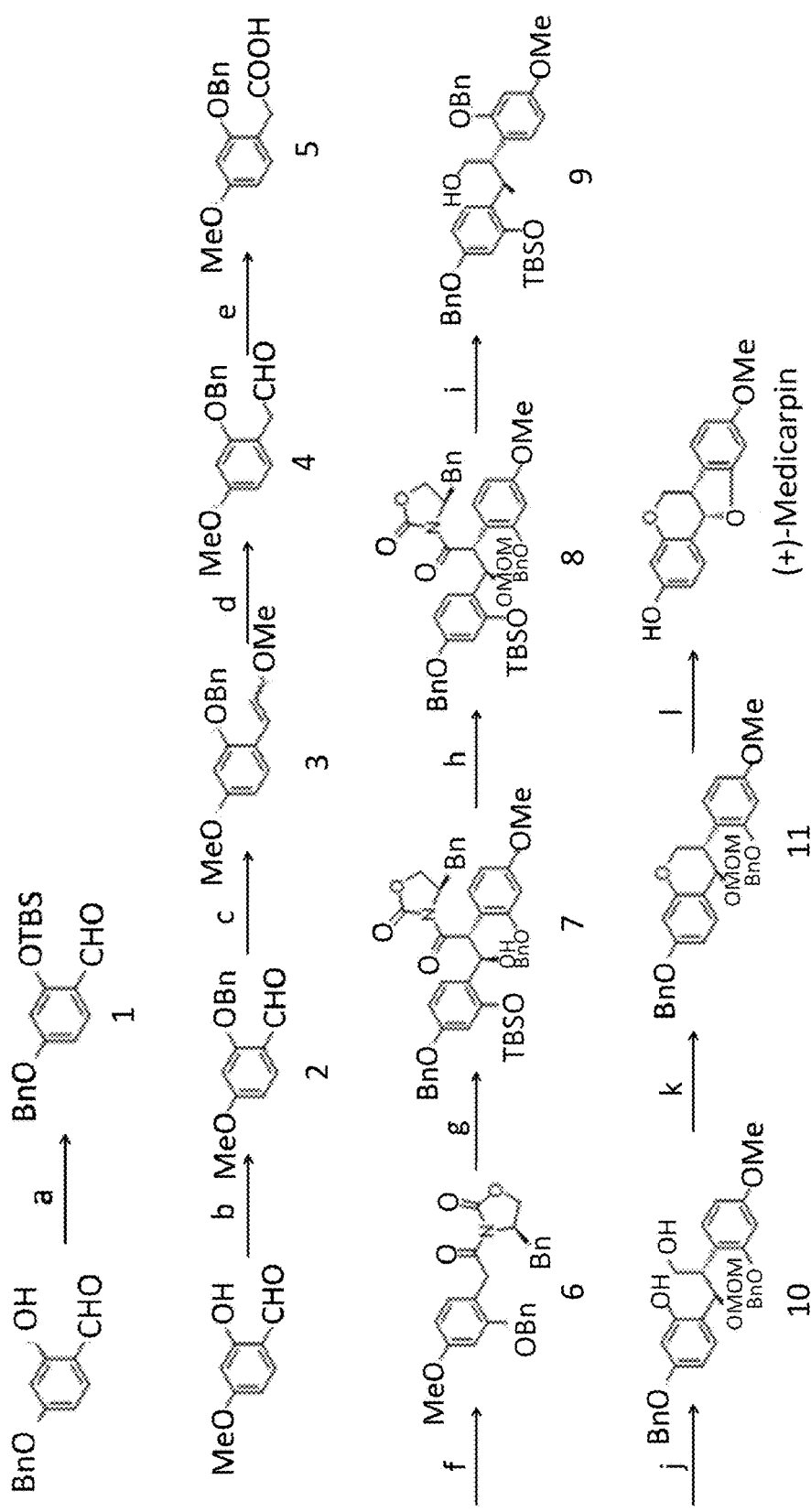
FIG. 1 is a schematic diagram showing the synthesis method of (+)-medicarpin.

In another embodiment, medicarpin and derivatives thereof can be synthesized by the following steps (a) to (1) (FIG. 1).

In step (a), 4-Benzyloxy-2-(tert-butyldimethylsilyloxy)-benzaldehyde (compound 1) is synthesized.
Compound 1:

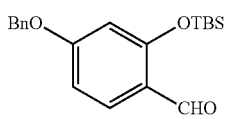

4-Benzyloxy-2-hydroxybenzaldehyde, imidazole, and TBSCl (tert-Butyl dim ethyl silyl chloride) are mixed in DMF (Dimethylformamide) and stirred. MeOH is then added and the mixture is stirred. Water is poured in and the resultant mixture is extracted with ether. The organic layers are combined and washed with water and brine, dried, and purified to obtain 4-Benzyloxy-2-(tert-butyldimethylsilyloxy)-benzaldehyde (compound 1).

In step (b), 2-Benzyloxy-4-methoxybenzaldehyde (compound 2) is synthesized.
Compound 2:

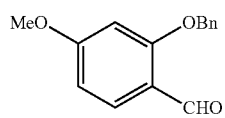

K$_2$CO$_3$ (Potassium carbonate) and BnBr (Benzyl bromide) are added to a solution of 4-methoxy-2-hydroxybenzaldehyde in acetonitrile. The mixture is cooled and the solvent is then removed. Water is added to the residue, which is extracted with Et$_2$O (Ether), brine, and dried. Recrystalization is performed to obtain 2-Benzyloxy-4-methoxybenzaldehyde (compound 2).

In step (c), methyl vinyl ether (compound 3) is synthesized.

Compound 3:

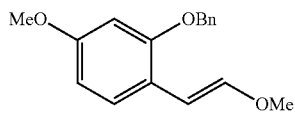

t-BuOK (Potassium tert-butoxide) is added in portions to (Methoxymethyl)triphenylphosphonium chloride in anhydrous THF (Tetrahydrofuran). Compound 2 in anhydrous THF is added dropwise, and the mixture is further stirred and sat. NH$_4$Cl (Ammonium chloride) is added to quench the reaction. EtOAc (Ethyl acetate) is used for extraction and the organic layers are washed with brine, and dried to obtain methyl vinyl ether (compound 3).

In step (d), 2-Benzyloxyl-4-methoxyphenylacetaldehyde (compound 4) is synthesized.
Compound 4:

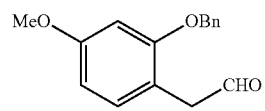

HCl (Hydrochloric acid) is added to a solution of compound 3 in THF. The mixture is cooled and sat. NaHCO$_3$ (sodium hydrogen carbonate) is added. Et$_2$O is used for extraction and the organic layers are washed with brine and dried. The solvent is removed and the residue is purified to obtain 2-Benzyloxyl-4-methoxyphenylacetaldehyde (compound 4).

In step (e), 2-Benzyloxyl-4-methoxyphenylacetic acid (compound 5) is synthesized.
Compound 5:

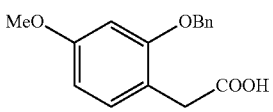

NaH$_2$PO$_4$ (Sodium dihydrogen phosphate) solution is added to compound 4, 2-methyl-2-butene, and NaClO$_2$ (Sodium chlorite). The mixture is stirred. The organic solvents are removed and the aqueous layer is extracted, dried, and purified to obtain 2-Benzyloxyl-4-methoxyphenylacetic acid (compound 5).

In step (f), imide (compound 6) is synthesized.
Compound 6:

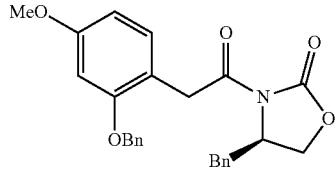

Oxalyl chloride and DMF are added to a solution of compound 5, and then stirred. The residue is dissolved in anhydrous THF to give an acyl chloride solution. In another flask, n-BuLi is added to R-4-benzyl-2-oxazolidinone in anhydrous THF. The acyl chloride solution is added dropwise to the reaction mixture and stirred. Saturated aqueous NH₄Cl is added and the mixture is extracted, washed, dried, and triturated with EtOAc and Hexane to obtain imide (compound 6).

In step (g), alcohol (compound 7) is synthesized.
Compound 7:

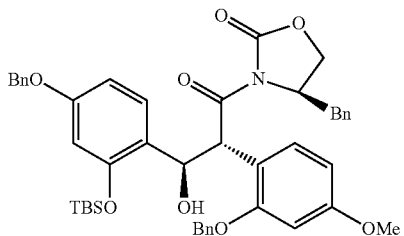

DIPEA (N,N-Diisopropylethylamin) (3.70 ml, 21 mmol) and Bu₂BOTf (Dibutylboranylium trifluoromethanesulfonate) are added to a stirred solution of compound 6 in anhydrous CH₂Cl₂ (Dichloromethane). The compound 1 in anhydrous CH₂Cl₂ is warmed to room temperature and stirred, and then quenched by addition of pH 7 buffer, followed by slow addition of MeOH/35% H₂O₂. The organic solvent is removed and ether is used for extraction. The organic layers are washed, and dried to obtain alcohol (compound 7).

In step (h), MOM (methoxymethyl) protected alcohol (compound 8) is synthesized.
Compound 8:

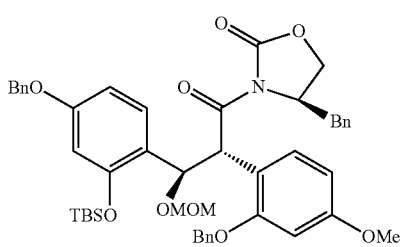

MOMCl (Chloromethyl methyl ether) is added dropwise to compound 7 and DIPEA (4.34 ml) in anhydrous CH₂Cl₂. TLC (Thin Layer Chromatography) indicated the reaction is not complete and an additional MOMCl (2.00 ml) and DIPEA are added and then stirred. Water is added and the mixture is stirred, extracted, and washed to obtain compound MOM protected alcohol (compound 8).

In step (i), MOM protected alcohol (compound 9) is synthesized.
Compound 9:

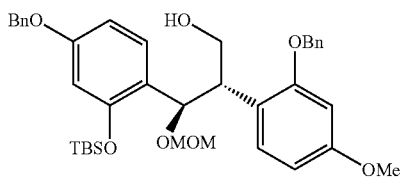

LiBH₄ (Lithium borohydride, LiBH₄) is added to compound 8 in aqueous Et₂O, and stirred. The reaction is quenched with NaOH and stirred. The solution is extracted with Et₂O, washed, and dried to obtain alcohol (compound 9).

In step (j), diol (compound 10) is synthesized.
Compound 10:

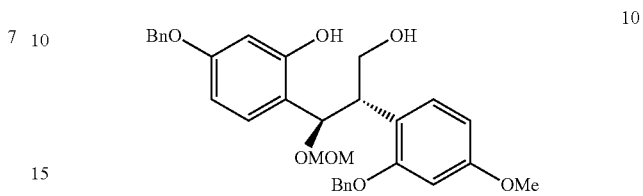

TBAF (Tetra-n-butylammonium fluoride) is added to a solution of compound 9 in THF. Water is added and EtOAc is used for extraction. The organic layers are combined and washed, and dried to obtain diol (compound 10).

In step (k), either (compound 11) is synthesized.
Compound 11:

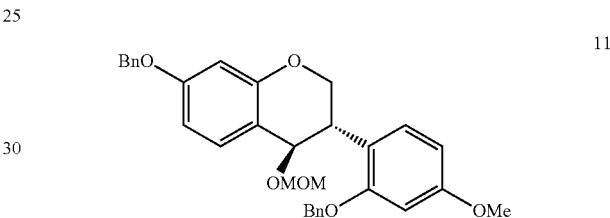

DEAD (Diethyl diazenedicarboxylate) is added to diol (compound 10) and PPh₃ (Triphenylphosphine). The mixture is loaded onto silica gel and purified to obtain either (compound 11).

In step (1), medicarpin (compound 12) is synthesized.
Compound 12:

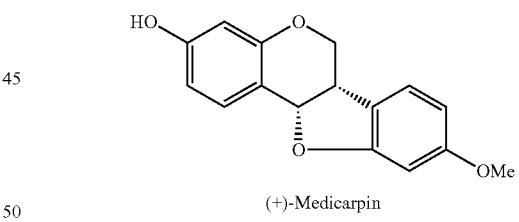

(+)-Medicarpin

A solution of ether (compound 11) and 10% Pd/C in EtOAc/MeOH is hydrogenated. The catalyst is filtered off with celite and the solvent is removed to give a white foam, which is dissolved in anhydrous CH₂Cl₂. Camphosulfonic acid (CSA) is added and the mixture is stirred. NaHCO₃ is added and the mixture is extracted and dried to obtain medicarpin.

Figure 2:
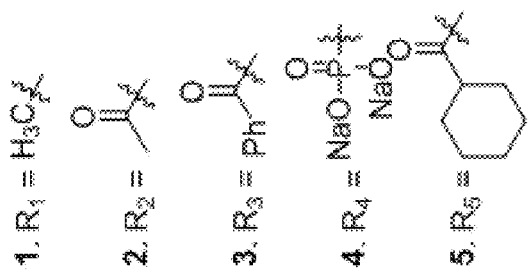
FIG. 2 illustrates the derivates of medicarpin and the preparation thereof.
Figure 2:
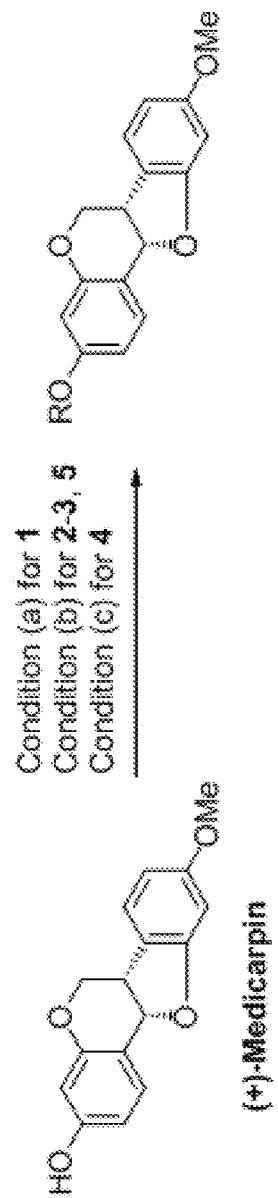

The present invention further provides the medicarpin's derivatives including derivative compounds 1, 2, 3, 4 and 5 as shown in FIG. 2. The synthesis of derivative compounds 1 to 5 is shown as follows.

Condition (a): CH₃I (Iodomethane) is added to a solution of Medicarpin and K₂CO₃ (Potassium carbonate) in acetone. The mixture is stirred overnight, loaded onto silica gel and separated to obtain derivative compound 1.

Condition (b): Acyl chloride is added to a solution of Medicarpin and TEA (2,2',2"-Nitrilotriethanol) in $CH_2Cl_2$ (Dichloromethane). The mixture was stirred and purified to obtain derivative compounds 2, 3, and 5.

Condition (c): $CCl_4$ (Carbon tetrachloride) is added to a solution of Medicarpin in $CH_3CN$ (Ethanenitrile). The mixture is stirred, and TEA and DMAP (4-Dimethylaminopyridine) are added. After 5 min, dibenzyl is added and the mixture is warmed to room temperature and stirred. $KH_2PO_4$ (Potassium dihydrogen phosphate) is added and EtOAc is used for extraction. Flash chromatography gave the phosphate ester, which is then dissolved in MeOH. Pd/C (Palladium on carbon) is added and the mixture is hydrogenated at balloon pressure overnight. The catalyst is removed by filtration and the filtrate is concentrated. MeOH and NaOMe (Sodium methoxide) are added and the mixture is stirred overnight. The solvent is removed under vacuum and the solid is filtered, washed with a small amount of cold water, cold MeOH, and ether to obtain derivative compound 4.

In another aspect of the invention, the prevent invention further provides a pharmaceutical composition comprising the compound of formula I and a pharmaceutical acceptable salt and carrier. The compound of formula I includes, but is not limited to, medicarpin (compound 12) and its derivatives (derivatives compounds 1 to 5).

The pharmaceutically acceptable carrier can include solvents, dispersion media, coatings, antibacterial and antifungal agents, isotonic and absorption delaying agents, and the like. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active azaazulene compound. Examples of other carriers include colloidal silicon oxide, magnesium stearate, cellulose, sodium lauryl sulfate, and D&C Yellow #10 (2-(2-Quinolyl)-1,3-indandione disulfonic acid disodium salt).

Suitable salts for the components to be employed according to the present subject matter are also those with inorganic cations, for example alkali metal salts, in particular sodium, potassium, or ammonium salts, alkaline earth metal salts such as, in particular, the magnesium or calcium salts, as well as salts with bi- or tetravalent cations, for example the zinc, aluminum, or zirconium salts. Also contemplated are salts with organic bases, such as dicyclohexylamine salts; methyl-D-glucamine; and salts with amino acids, such as arginine, lysine, histidine, glutamine and so forth. Also, the basic nitrogen-containing groups can be quaternized with such agents as: lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others. Salt-forming agents, for example, low molecular weight alkylamines such as methylamine, ethylamine, or triethylamine can also be employed. Water or oil-soluble or dispersible products are thereby obtained.

To practice the treatment method of the invention, a composition having one or more medicarpin and/or derivative thereof can be administered to a subject (e.g., a mammal) parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

In another aspect of the invention, the present invention provides a method for treating renal and cardiac dysfunction, comprising administrating the pharmaceutical composition of the present invention to a subject.

The renal and cardiac dysfunction includes, but is not limited to, ischaemic disease, cardiomyopathy, and heart failure.

The subject in the present invention is desirably a human patient, although it is to be understood that the principles of the invention indicate that the invention is effective with respect to all mammals. The mammal is understood to include any mammalian species in which treatment of tissue associated with diseases involving angiogenesis is desirable, particularly agricultural and domestic mammalian species.

Medicarpin or its derivatives can enhance the erythropoietin activity of bone marrow, and stimulate the proliferation and differentiation of erythroid progenitor cells. The number of red blood cell (RBC), white blood cell (WBC) and platelet (PLT), and the amount of hemoglobin (HGB) can be recovered by medicarpin or its derivatives. Medicarpin or its derivatives is an inducer of endogenous EPO expression in the heart, kidney and liver, and treat and prevent cardiac dysfunction including ischaemic heart disease, cardiomyopathy, and heart failure.

Example 1

Synthesis of (+)-Medicarpin

Referring to FIG. 1, the synthesis method of (+)-Medicarpin was describe as follow steps (a)-(l).

Step (a). 4-Benzyloxy-2-(tert-butyldimethylsilyloxy)-benzaldehyde

4-Benzyloxy-2-hydroxybenzaldehyde (11.40 g, 50 mmol), imidazole (3.74 g, 55 mmol), and TBSCl (8.39 g, 54 mmol) were mixed in DMF (100 ml) and stirred at room temperature for 3 hours. MeOH was then added and the mixture was stirred for another 30 minutes. Water was poured in and the resultant mixture was extracted with ether. The organic layers were combined and washed with $H_2O$ and brine, dried over $MgSO_4$, and purified by flash chromatography to give compound 1 in quantitative yield as a colorless oil. $^1H$ NMR (400 MHz, $CDCl_3$): δ 10.28 (s, 1H), 7.79 (d, J=8.8 Hz, 1H), 7.40-7.33 (m, 5H), 6.68 (dd, J=8.8 Hz, 2.4 Hz, 1H), 6.37 (d, J=2.4 Hz, 1H), 5.10 (s, 2H), 0.99 (s, 9H), 0.22 (s, 6H); $^{13}C$ NMR (100 MHz, $CDCl_3$) δ 188.5, 164.7, 160.6, 135.9, 130.0, 128.7, 128.2, 127.2, 121.4, 108.8, 105.9, 70.2, 60.3, 25.6, 18.2, −4.4; ESI MS m/z calcd for $C_{21}H_{29}O_3Si$ 357.1886 $[M+CH_3+H]^+$, found 357.1886.

Step (b). 2-Benzyloxy-4-methoxybenzaldehyde

To a solution of 4-methoxy-2-hydroxybenzaldehyde (15.2 g, 100 mmol) in acetonitrile (200 ml) was added $K_2CO_3$ (16.56 g, 120 mmol) and BnBr (13.07 ml, 110 mmol), and the resultant solution was refluxed overnight. The mixture was cooled and the solvent was then removed under vacuum. To the residue was added $H_2O$ (100 ml), which was extracted with $Et_2O$, brine, and dried over $MgSO_4$. Recrystallization in MeOH gave compound 2 (22.50 g, 93%) as a white solid.

Step (c). Methyl vinyl ether t-BuOK (15.66 g, 139.5 mmol) was added in portions to (Methoxymethyl)triphenylphosphonium chloride (47.82 g, 139.5 mmol) in 300 ml of anhydrous THF at 0° C. under Ar. After 30 min, aldehyde 2 (22.50 g, 93 mmol) in 100 ml of anhydrous THF was added dropwise over 30 min, and the mixture was further stirred for another 30 min before sat. NH$_4$Cl was added to quench the reaction. EtOAc was used for extraction and the organic layers were washed with brine, dried over MgSO$_4$. Vinyl ether (compound 3) was obtained (25.06 g, 93%) as colorless oil by flash chromatography using EtOAc and hexane. $^1$H NMR (400 MHz, CDCl$_3$): cis+trans isomers δ 7.95 (d, J=8.0 Hz, 0.36OH), 7.44-7.31 (m, 4.40H), 7.15 (d, J=8.0 Hz, 0.52H), 7.02 (d, J=12.0 Hz, 0.48H), 6.50-6.44 (m, 2H), 6.08 (d, J=8.0 Hz, 0.400H), 6.01 (d, J=12.0 Hz, 0.49H), 5.63 (d, J=8.0 Hz, 0.38H), 5.07 (s, 1.12H), 5.04 (s, 0.88H), 3.36-3.37 (m, 3H), 3.73 (s, 1.32H), 3.62 (s, 1.68H); $^{13}$C NMR (100 MHz, CDCl$_3$) cis+trans isomers δ 158.8, 158.6, 156.0, 155.8, 148.3, 146.3, 137.1, 137.0, 130.2, 128.5, 128.4, 127.8, 127.7, 127.2, 127.2, 127.2, 126.7, 118.4, 118.1, 105.1, 104.7, 100.7, 100.2, 99.6, 98.6, 70.3, 70.2, 60.3, 56.4, 55.3, 55.3; ESI MS m/z calcd for C$_{17}$H$_{19}$O$_3$ 271.1334 [M+H]$^+$, found 271.1330.

Step (d).
2-Benzyloxyl-4-methoxyphenylacetaldehyde

To a solution of ether 3 (compound 3) (13.52 g, 50 mmol) in 200 ml of THF was added 3N HCl (15 ml), which was refluxed for 1 h. The mixture was cooled to room temperature and sat. NaHCO$_3$ (100 ml) was added. Et$_2$O was used for extraction and the organic layers were washed with brine, dried over MgSO$_4$. The solvent was removed in vacuo and the residue was purified by flash chromatography to obtain compound 4 (11.05 g, 86%) as a light yellow oil. $^1$H NMR (400 MHz, CDCl$_3$): δ 9.67 (s, 1H), 7.37-7.29 (m, 5H), 7.05 (d, J=8.0 Hz, 1H), 6.55 (s, 1H), 6.48 (d, J=8.0 Hz, 1H), 5.04 (s, 2H), 3.77 (s, 3H), 3.61 (s, 2H); $^{13}$C NMR (100 MHz, CDCl$_3$) δ 200.3, 160.4, 157.5, 136.5, 131.6, 128.6, 127.9, 127.2, 127.2, 113.7, 104.8, 99.9, 70.1, 55.3, 44.8; ESI MS m/z calcd for C$_{16}$H$_{17}$O$_3$ 257.7718 [M+H]$^+$, found 257.7738.

Step (e). 2-Benzyloxyl-4-methoxyphenylacetic Acid

At 0° C., NaH$_2$PO$_4$ (6.21 g, 51.74 mmol) in 40 ml of H$_2$O was added to aldehyde 4 (compound 4) (11.05 g, 43.11 mmol), 2-methyl-2-butene (18.14 g, 258.66 mmol), and NaClO$_2$ (tech. 80%, 5.85 g, 51.74 mmol) in t-BuOH/THF (1:1, 200 ml). The ice bath was removed after 30 min and the mixture was stirred for 3 h. The organic solvents were removed in vacuo and the aqueous layer was extracted with CH$_2$Cl$_2$, dried over MgSO$_4$. Compound 5 was purified by recrystallization in EtOAc/hexane and obtained (9.50 g, 81%) as a white solid. Mp=114.0-116° C. $^1$H NMR (400 MHz, CDCl$_3$): δ 7.35-7.26 (m, 5H), 7.10 (d, J=8.0 Hz, 1H), 6.50 (d, J=2.4 Hz, 1H), 6.46 (dd, J=8.0, 2.4 Hz, 1H), 3.76 (s, 3H), 3.63 (s, 2H); $^{13}$C NMR (100 MHz, CDCl$_3$) δ 177.6, 160.2, 157.3, 136.6, 131.3, 128.5, 127.8, 127.0, 115.1, 104.6, 99.9, 70.0, 55.3, 35.2; ESI MS m/z calcd for C$_{16}$H$_{17}$O$_4$ 273.1127 [M+H]$^+$, found 273.1120.

Step (f). Imide

To a solution of acid 5 (Compound 5) (10.64 g, 39.07 mmol) in anhydrous CH$_2$Cl$_2$ (100 ml) was added oxalyl chloride (7 ml) and DMF (catalytic), which was then stirred at room temperature for 1 h and evaporated. The residue was dissolved in anhydrous THF to give an acyl chloride solution. In another flask, n-BuLi (2.5 M, 16.4 ml, 41 mmol) was added to R-4-benzyl-2-oxazolidinone (7.09 g, 40 mmol) in anhydrous THF (160 ml) at −78° C., which was warmed to 0° C., stirred for an additional 30 min, and then recooled to −78° C. The acyl chloride solution was added dropwise to the reaction mixture and stirred at the same temperature for 1 h before being warmed to room temperature and stirred for 2 h. Saturated aqueous NH$_4$Cl was added and the mixture was extracted with EtOAc, washed with brine and dried over MgSO$_4$, triturated with EtOAc and Hexane to give compound 6 (13.30 g, 79%) as a light yellow solid. Mp=108.0-110.0° C. $[α]^{23}_D$=−52.2° (c 0.12, MeOH). $^1$H NMR (400 MHz, CDCl$_3$): δ 7.40-7.25 (m, 8H), 7.13-7.09 (m, 3H), 6.55 (d, J=2.4 Hz, 1H), 6.50 (dd, J=8.0 Hz, 2.4 Hz, 1H), 5.03 (s, 2H), 4.54-4.48 (m, 1H), 4.22 (d, J=2.8 Hz, 2H), 4.04 (dd, J=8.8 Hz, 2.8 Hz, 1H), 3.97 (t, J=8.0 Hz, 1H), 3.79 (s, 3H), 3.19 (dd, J=13.4 Hz, 2.8 Hz, 1H), 2.47 (dd, J=13.4 Hz, 10.0 Hz, 1H); $^{13}$C NMR (100 MHz, CDCl$_3$) δ 171.5, 160.2, 157.4, 153.5, 136.9, 135.5, 131.5, 129.3, 128.8, 128.8, 128.5, 127.9, 127.4, 127.1, 115.7, 104.5, 99.8, 70.8, 66.1, 55.4, 55.3, 37.6, 36.8; ESI MS m/z calcd for C$_{26}$H$_{26}$NO$_5$ 432.1811 [M+H]$^+$, found 432.1817.

Step (g). Alcohol

To a stirred solution of Imide 6 (compound 6) (7.56 g, 17.52 mmol) in anhydrous CH$_2$Cl$_2$ (100 ml) was added DIPEA (3.70 ml, 21 mmol) and Bu$_2$BOTf (1M in CH$_2$Cl$_2$, 20 ml) at −78° C., which was warmed to 0° C. and stirred for an additional 1 h. The aldehyde 1 (6.60 g, 19.27 mmol) in anhydrous CH$_2$Cl$_2$ was added dropwise and the resultant mixture was stirred at −78° C. for 1 h. The reaction was warmed to room temperature and stirred overnight, and then quenched by addition of pH 7 buffer (25 ml), followed by slow addition of MeOH/35% H$_2$O$_2$ (v:v=2:1, 50 ml) with ice bath and further stirring at room temperature for 1 h. The organic solvent was removed under vacuum and ether was used for extraction. The organic layers were washed with sat. NaHCO$_3$ and dried over MgSO$_4$. Flash chromatography gave compound 7 (10.31 g, 76%) as a white solid. Mp=74.0-76.0° C. $[α]^{23}_D$=+70.3° (c 0.15, MeOH). $^1$H NMR (400 MHz, CDCl$_3$): δ 7.39-7.24 (m, 13H), 7.11-7.09 (m, 3H), 6.76 (d, J=8.0 Hz, 1H), 6.41 (ddd, J=15.6, 8.4, 2.4 Hz, 2H), 6.30 (d, J=2.4 Hz, 1H), 6.12 (d, J=2.4 Hz, 1H), 5.59 (s, 2H), 4.92 (s, 2H), 4.81 (d, J=12.0 Hz, 1H), 4.64-4.58 (m, 1H), 4.53 (d, J=12.0 Hz, 1H), 3.96-3.95 (m, 2H), 3.71 (s, 3H), 3.67 (d, J=2.4 Hz, 1H), 3.28 (dd, J=13.4 Hz, 2.8 Hz, 1H), 2.42 (dd, J=13.4 Hz, 10.0 Hz, 1H), 0.94 (s, 9H), 0.13 (s, 6H); $^{13}$C NMR (100 MHz, CDCl$_3$) δ 175.2, 160.2, 158.7, 158.6, 153.2, 152.1, 137.5, 137.4, 135.6, 131.2, 129.6, 129.1, 128.7, 128.5, 128.2, 128.1, 127.7, 127.6, 127.5, 127.4, 127.2, 124.6, 114.6, 106.9, 105.4, 104.2, 100.0, 70.4, 70.1, 68.8, 66.1, 55.4, 55.4, 48.1, 37.8, 26.0, 18.3; ESI MS m/z calcd for C$_{46}$H$_{51}$NNaO$_8$Si 796.3286 [M+Na]$^+$, found 796.3276.

Step (h). MOM Protected Alcohol

MOMCl (2.00 ml) was added dropwise to alcohol 7 (compound 7)(5.96 g, 7.70 mmol) and DIPEA (4.34 ml) in anhydrous CH$_2$Cl$_2$ (50 ml) at 0° C., which was warmed to room temperature overnight. TLC indicated the reaction was not complete and an additional MOMCl (2.00 ml) and DIPEA (4.34 ml) were added, which was stirred overnight. H$_2$O was added and the mixture was stirred for 10 min, extracted with CH$_2$Cl$_2$, washed with brine. Flash chromatography gave compound 8 (5.23 g, 83%) as a light yellow oil. $[α]^{23}_D$=+77.4° (c 0.09, MeOH). $^1$H NMR (400 MHz, CDCl$_3$) δ 7.59 (d, J=8.0 Hz, 1H), 7.44 (d, J=8.0 Hz, 2H), 7.36-7.26 (m, 8H), 7.24-7.19 (m, 4H), 7.00 (dd, J=7.2, 1.2 Hz, 2H), 6.54 (td, J=9.0, 2.4 Hz, 2H), 6.45 (d, J=2.4 Hz, 1H), 6.25 (d, J=2.4 Hz, 1H), 6.04 (d, J=8.8 Hz, 1H), 5.63 (d, J=8.8 Hz, 1H), 5.04-4.96 (m, 2H), 4.94 (s, 2H), 4.45 (d, J=8.8 Hz, 1H), 4.36 (d, J=8.8 Hz, 1H), 4.17-4.11 (m, 1H), 3.75 (s, 3H), 3.71 (dd, J=8.8, 2.4 Hz, 2H), 3.46 (t, J=8.0 Hz, 1H), 3.09 (dd, J=13.2 Hz, 3.2 Hz, 1H), 3.03 (s, 3H), 2.11 (dd, J=13.2, 10.4 Hz, 1H), 1.05 (s, 9H), 0.22 (d, J=2.8 Hz, 6H); $^{13}$C NMR (101 MHz, CDCl$_3$) δ 171.8, 159.8, 159.0, 158.1, 154.6, 152.2, 137.2, 136.9, 135.9, 130.1, 129.9, 129.3, 128.7, 128.5, 128.3, 127.9, 127.5, 127.5, 127.4, 126.9, 122.8, 118.0, 107.1, 104.9, 104.5, 99.9, 94.1, 71.9, 70.4), 69.9, 65.4, 55.9, 55.6, 55.2, 46.8, 37.3, 34.6, 25.8, 18.2; ESI MS m/z calcd for C$_{48}$H$_{55}$NNaO$_9$Si 840.3544 [M+Na]$^+$, found 840.3528.

Step (i). Alcohol

LiBH$_4$ (4M in THF, 2.00 ml) was added to alcohol 8 (compound 8)(5.23 g, 6.40 mmol) in aqueous Et$_2$O (50 ml, plus 0.1 ml H$_2$O) at room temperature, which was stirred for 1 h. The reaction was quenched with 1N NaOH (30 ml) and stirred for an additional 1 h. The solution was extracted with Et$_2$O, washed with brine and dried. Flash chromatography gave compound 9 (2.51 g, 61%) as a colorless oil. [α]$^{23}_D$= +141.5° (c 0.07, MeOH). $^1$H NMR (400 MHz, CDCl$_3$): δ 7.42-7.29 (m, 11H), 7.00 (d, J=8.4 Hz, 1H), 6.50 (dt, J=8.8, 2.4 Hz, 2H), 6.39 (d, J=2.4 Hz, 1H), 6.34 (d, J=2.4 Hz, 1H), 5.42 (d, J=6.4 Hz, 1H), 4.98 (s, 2H), 4.93 (d, J=12.4 Hz, 1H), 4.81 (d, J=12.4 Hz, 1H), 4.40 (dd, J=16.4 Hz, 8.4 Hz, 2H), 3.81-3.78 (m, 2H), 3.75 (s, 3H), 3.73-3.71 (m, 1H), 3.13 (s, 3H), 1.01 (s, 9H), 0.18 (d, J=4.4 Hz, 6H); $^{13}$C NMR (100 MHz, CDCl$_3$) δ 159.3, 158.8, 158.1, 154.5, 137.5, 137.1, 129.8, 129.2, 128.7, 128.5, 128.1, 127.7, 127.6, 127.3, 123.7, 120.9, 107.8, 105.7, 104.8, 100.1, 94.2, 72.1, 70.3, 70.2, 64.5, 55.6, 55.4, 44.8, 29.9, 26.0, 18.4; ESI MS m/z calcd for C$_{38}$H$_{48}$NaO$_7$Si 667.3067 [M+Na]$^+$, found 667.3055.

Step (j). Diol

To a solution of alcohol 9 (compound 9)(2.51 g, 3.89 mmol) in THF (20) was added TBAF (1M in THF, 5 ml). After 1 h, water was added and EtOAc was used for extraction. The organic layers were combined and washed with brine, dried over MgSO$_4$. Flash chromatography gave compound 10 (1.99 g, 96%) as a colorless oil. [α]$^{23}_D$= +188.0° (c 0.08, MeOH). $^1$H NMR (400 MHz, CDCl$_3$) δ 7.41-7.30 (m, 10H), 7.20 (d, J=8.4 Hz, 1H), 6.85 (d, J=8.4 Hz, 1H), 6.53-6.48 (m, 3H), 6.42 (dd, J=8.4, 2.4 Hz, 1H), 5.15 (d, J=8.4 Hz, 1H), 5.00-4.98 (m, 4H), 4.54 (d, J=6.8 Hz, 1H), 4.37 (d, J=6.8 Hz, 1H), 3.76 (s, 3H), 3.67-3.62 (m, 3H), 2.96 (s, 3H); $^{13}$C NMR (100 MHz, CDCl$_3$) δ 159.8, 159.7, 157.8, 156.7, 136.9, 136.6, 129.7, 128.6, 128.5, 128.0, 127.9, 127.6, 127.5, 120.4, 116.8, 106.9, 104.7, 103.4, 100.1, 94.1, 70.4, 69.9, 63.4, 55.8, 55.3; ESI MS m/z calcd for C$_{32}$H$_{34}$NaO$_7$ 553.2202 [M+Na]$^+$, found 553.2188.

Step (k). Ether

To diol 10 (compound 10)(1.99 g, 3.73 mmol) and PPh$_3$ (1.18 g, 4.50 mmol) in 30 ml of anhydrous THF was added DEAD (40 wt % in toluene, 2.10 ml, 4.60 mmol), and TLC indicated the reaction was complete after about 30 min. The mixture was loaded onto silica gel and purified by flash chromatography to give compound 11 (1.83 g, 96%) as a colorless oil. [α]$^{24}_D$=−21.5° (c 0.13, MeOH). $^1$H NMR (400 MHz, CDCl$_3$): δ 7.46-7.29 (m, 10H), 7.14 (d, J=8.4 Hz, 1H), 7.04 (d, J=8.4 Hz, 1H), 6.57 (dd, J=8.4 Hz, 2.4 Hz, 1H), 6.50 (dd, J=9.6 Hz, 2.4 Hz, 2H), 6.32 (dd, J=8.4 Hz, 2.4 Hz, 1H), 5.08 (s, 2H), 5.01 (s, 2H), 4.70-4.68 (m, 2H), 4.62 (d, J=8.4 Hz, 1H), 4.47 (dd, J=11.2 Hz, 3.2 Hz, 1H), 4.45 (dd, J=11.2, 3.2 Hz, 1H), 3.72 (s, 3H), 3.62-3.60 (m, 1H), 3.30 (s, 3H); $^{13}$C NMR (100 MHz, CDCl$_3$) δ 160.3, 159.6, 157.1, 151.3, 136.8, 136.7, 130.2, 128.5, 127.9, 127.9, 127.7, 127.5, 127.2, 123.9, 119.9, 115.8, 108.7, 105.4, 103.0, 100.6, 98.6, 90.9, 70.5, 70.1, 55.4, 55.0, 25.6, 14.4; ESI MS m/z calcd for C$_{30}$H$_{27}$O$_4$ 451.1909 [M−MOM−H$_2$O+H]$^+$, found 451.1908.

Step (l). (+)-Medicarpin

A solution of ether 11 (compound 11) (1.83 g, 3.57 mmol) and 10% Pd/C (400 mg) in EtOAc/MeOH (1:3, 30 ml) was hydrogenated at balloon pressure overnight. The catalyst was filtered off with celite and the solvent was removed under vacuum to give a white foam, which was dissolved in anhydrous CH$_2$Cl$_2$ (30 ml). Camphosulfonic acid (20 mg) was added and the mixture was stirred at room temperature for 30 min. Sat. NaHCO$_3$ was added and the mixture was extracted with CH$_2$Cl$_2$, drived over MgSO$_4$. Flash chromatography gave (+)-medicarpin (533 mg, 55%) as a white solid over two steps. Mp=131.0-133.0° C. (lit. 132.0-133.5° C.[7,28], 125.0-127.0° C.[5]); [α]$^{23}_D$=+223.6° (c 0.15, MeOH) (lit [α]$^{20}_D$=+223.1° (c 0.16, acetone))[7,28]; $^1$H NMR (400 MHz, CDCl$_3$): δ 7.39 (d, J=8.8 Hz, 1H), 7.13 (d, J=8.8 Hz, 1H), 6.55 (dd, J=8.0 Hz, 2.4 Hz, 1H), 6.46-6.44 (m, 2H), 6.41 (d, J=2.4 Hz, 1H), 5.50 (d, J=6.8 Hz, 1H), 4.93 (s, 1H), 4.24 (dd, J=11.2 Hz, 4.8 Hz, 1H), 3.76 (s, 3H), 3.62 (t, J=10.8 Hz, 1H), 3.55-3.50 (m, 1H); $^{13}$C NMR (101 MHz, CDCl$_3$) δ 161.3, 160.8, 157.3, 156.8, 132.4, 125.0, 119.3, 112.8, 110.0, 106.7, 103.9, 97.1, 78.8, 66.7, 55.7, 39.7; ESI MS m/z calcd for C$_{16}$H$_{13}$O$_4$ 269.0814 (M−H)$^−$, found 269.0819.

Example 2

Synthesis of (+)-Medicarpin Derivatives

The (+)-Medicarpin derivates and the synthesis method thereof were described in FIG. 2.

a. Synthesis Method of Derivative Compound 1(YXM-M1)

To a solution of (+)-Medicarpin (27 mg, 0.10 mmol) and K$_2$CO$_3$ (28 mg, 0.20 mmol) in acetone (5 ml) was added CH$_3$I (12 μl, 0.20 mmol). The mixture was stirred overnight at room temperature, which was loaded onto silica gel and separated by flash chromatography to give derivative compound 1(YXM-M1) (24 mg, 84%) as a white solid.

b. Synthesis Method of Derivative Compounds 2-3 and 5(YXM-M2-3,5)

To a solution of (+)-Medicarpin (27 mg, 0.10 mmol) and TEA (21 μl, 0.15 mmol) in CH$_2$Cl$_2$ (5 ml) was added acyl chloride (0.15 mmol) at room temperature. The mixture was stirred for 1 to 2 hours as monitored by TLC and purified by flash chromatography to give derivative compounds 2, 3, and 5 (YXM-M2-3,5) as white solids (Yield: >90%).

c. Synthesis Method of Derivative Compound 4(YXM-M4)

To a solution of (+)-Medicarpin (54 mg, 0.20 mmol) in CH$_3$CN (5 ml) was added CCl$_4$ (0.17 ml, 1.76 mmol) at −20°

C. The mixture was stirred for 10 min, and TEA (56 µl, 0.40 mmol) and DMAP (2.5 mg, 0.02 mmol) were added. After 5 min, dibenzyl phosphite (83 µl, 0.30 mmol) was added and the mixture was warmed to room temperature and stirred for 1 h. $KH_2PO_4$ (10 ml, 0.5N) was added and EtOAc was used for extraction. Flash chromatography gave the phosphate ester as a colorless foam (87 mg, 82%, 0.164 mmol), which was then dissolved in MeOH. Pd/C (20 mg) was added and the mixture was hydrogenated at balloon pressure overnight. The catalyst was removed by filtration and the filtrate was concentrated. MeOH (5 ml) and NaOMe (77 µl, 0.328 mmol) were added and the mixture was stirred overnight. The solvent was removed under vacuum and the solid was filtered, washed with a small amount of cold water, cold MeOH, and ether to give the salt (derivative compound 4) (YXM-M4) as an off-white solid (34 mg, 43% over 3 steps).

Example 3

Figures 1, 3A:
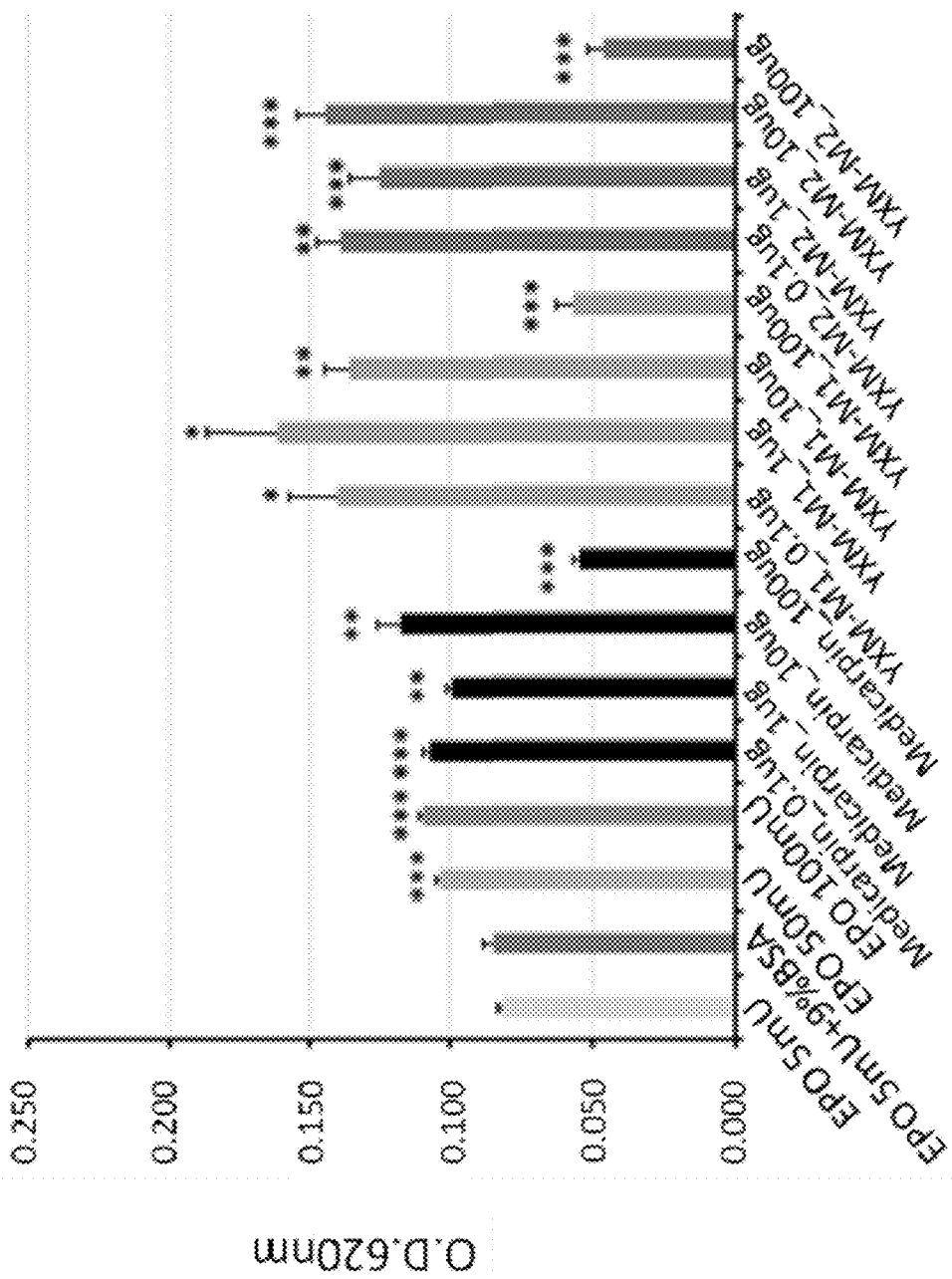
Figures 2, 3A:
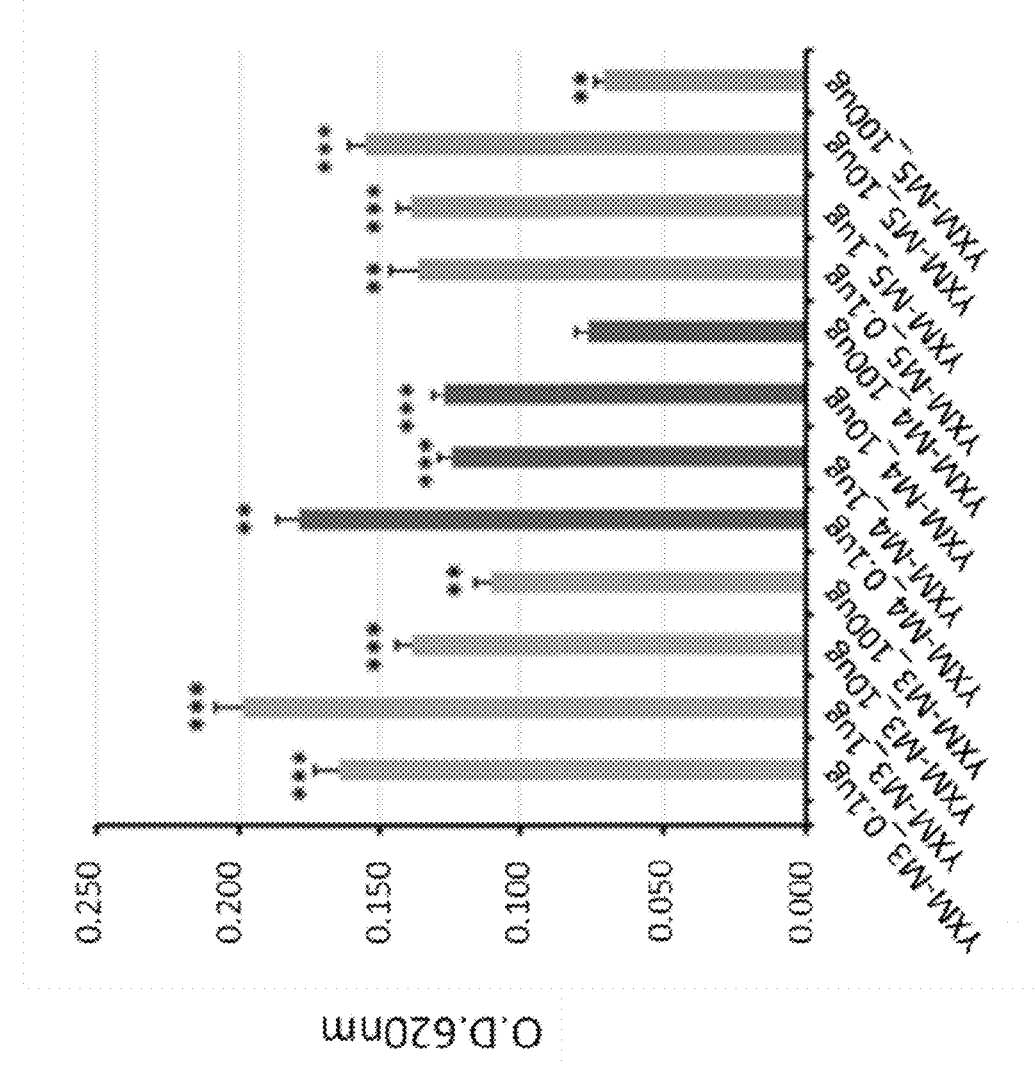
Figure 3B:
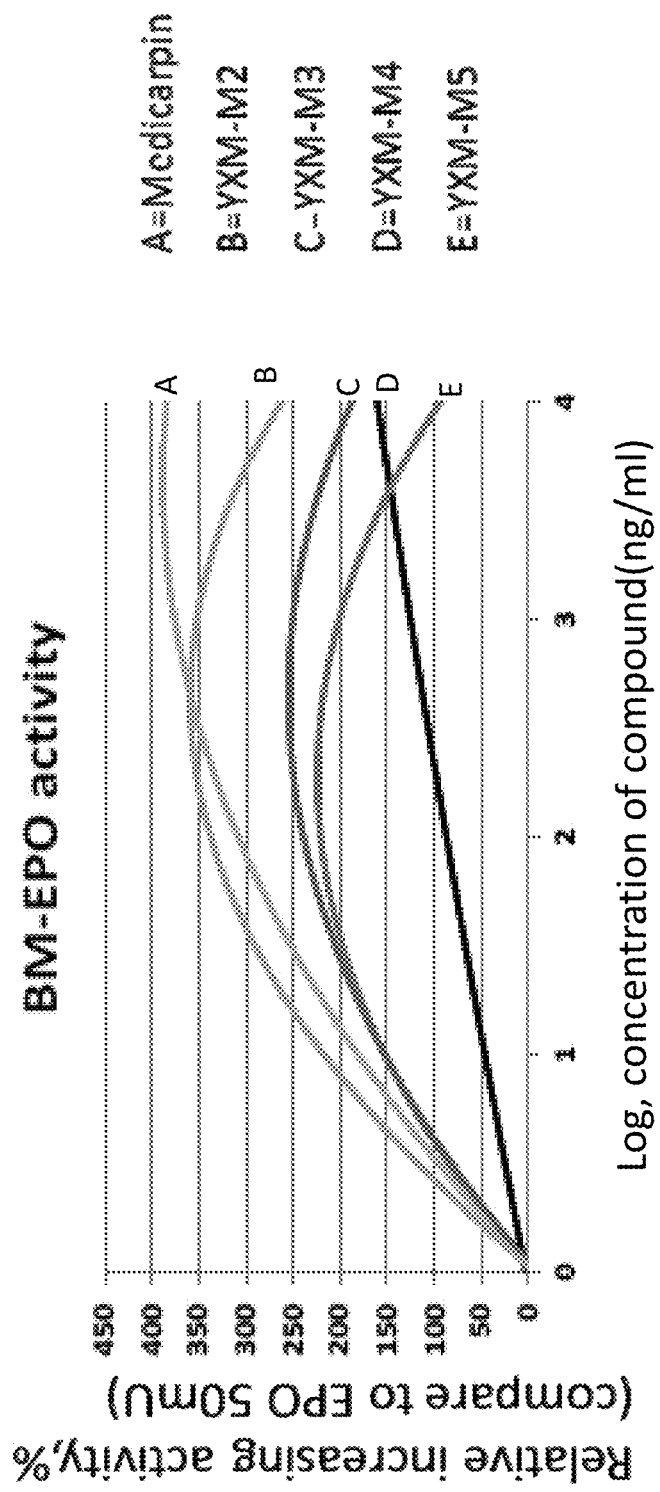

Effect of (+)-Medicarpin on Erythroid Precursor Cells a. Isolation of Bone Marrow Cells C57BL/6J male mice (6 weeks old) were used in this Example to collect bone marrow cells. The hind legs were of mice were obtained to remove excess flesh from the leg bone and cut off the ends of the bones. The bones were flushed with α-MEM medium using 23-gauge needle to elute bone marrow cells, and then filtrated by No. 53 nylon mesh filter to obtain the bone marrow cells solution. The cells solution was centrifuged at 1450 rpm (Kubota 5010) for 5 minutes, and then re-suspended in α-MEM medium containing 10% FBS and 2 mM glutamine.

b. Bone Marrow Progenitor Cell Colony-Forming Assay $8.4 \times 10^4$/mL bone marrow cells were seeded in 24-wells plates and cultured with a α-MEM medium (15% FBS, 1% BSA, 0.8% methylcellulose, 0.1 mM β-mercaptoethanol, 2 U/mL rHuEPO, and 10 ng/mL IL-3) in a incubator at 37° C. and 5% $CO_2$ for 9 days. Colonies containing more than 50 individual cells were counted using a stereomicroscope.

c. Hemoglobin Colorimetric Assay $6 \times 10^5$/mL bone marrow cells were seeded in 96-wells plates and cultured with aα-MEM medium (1% BSA, 7.5 µM β-mercaptoethanol, 1.4 mM L-glutamate, 5 µM $FeCl_3$, and 25 mU/well rHuEPO). After 24 hours in a incubator at 37° C. and 5% $CO_2$ for 24 hours, and then treated with medicarpin, and derivatives compounds 1 to 5 (YXM-M1 to YXM-M5) for 96 hours. 96-well plates (U-bottom shape) were centrifuged at 1200 rpm (Kubota 6800) at 25° C. for 5 minutes. After centrifugation, the supernatant was removed and the bone marrow cells were mixed equally with 50 µL lysis buffer (0.01% NP-40) for 10 minutes. Then, 150 µL of 500 µM DAF (2,7-Diaminofluorene, Sigma-Aldrich) solution and 6 µL of 30% $H_2O_2$ were added and treated with the bone marrow cells for 5 minutes, and absorbance at 610 nm ($A_{610}$) was determined. Student's t-test were used to compare data. The results showed that the differentiation of erythroid progenitor cells was enhanced in the presence of a low concentration (0.1 to 10 µg/mL) of medicarpin (FIG. 3A-1,3A-2). The derivates of medicarpin, YXM-M1 (derivative compound 1), YXM-M2 (derivative compound 2), YXM-M3 (derivative compound 3), YXM-M4 (derivative compound 4), and YXM-M5 (derivative compound 5), also have the similar activities, the differentiation of erythroid progenitor cells was enhanced in the presence of a low concentration and the differentiation of erythroid progenitor cells was inhibited in the presence of a high concentration (100 µl/ml). except for YXM-M1. Further, the increasing activity ($EC_{1.5}$) of erythroid progenitor cells is shown in FIG. 3B, The result show that the derivatives of medicarpin, except for YXM-M1, has higher erythropoietin stimulating activity than the medicarpin. Particularly, YXM-M3 and YXM-M5 have the highest erythropoietin stimulating activity. The results indicated that the pterocarpans medicarpin could enhance erythropoietin activity of bone marrow, and stimulate the proliferation and differentiation of erythroid progenitor cells.

Example 4

Figure 4:
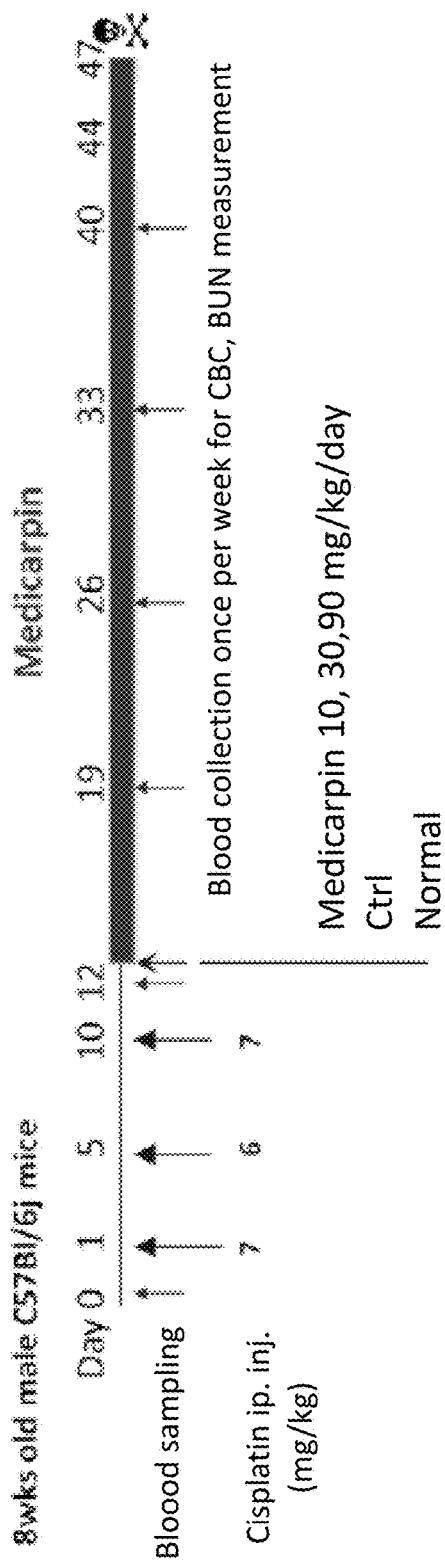
FIG. 4 is a schematic diagram showing the protocol to investigate the therapeutic effect of medicrpin in cisplatin-induced nephropathic mice.
Figure 5A:
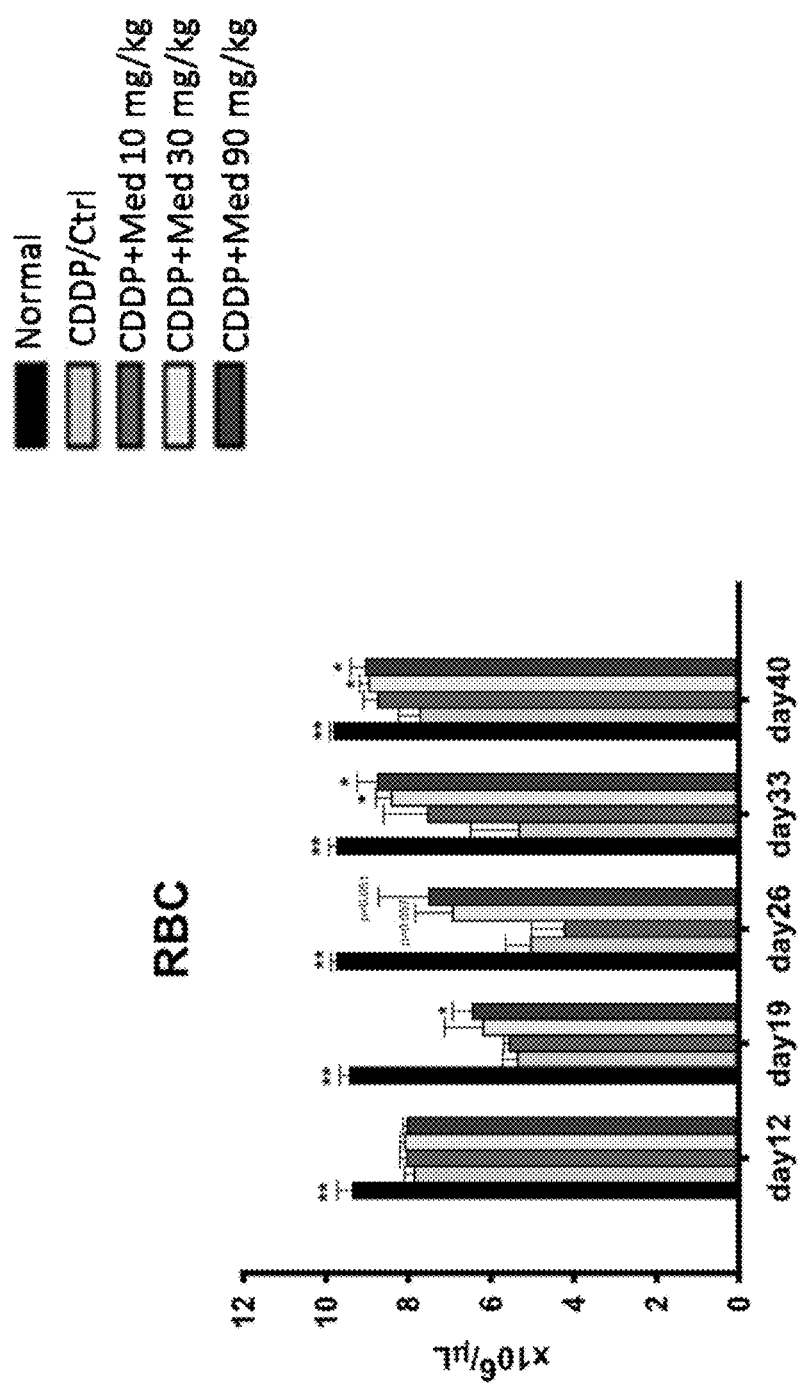
FIGS. 5A-5D are graphs showing the recovery of RBC (FIG. 5A), HGB (FIG. 5B), WBC (FIG. 5C), and platelet (FIG. 5D) number in the peripheral blood.
Figure 5B:
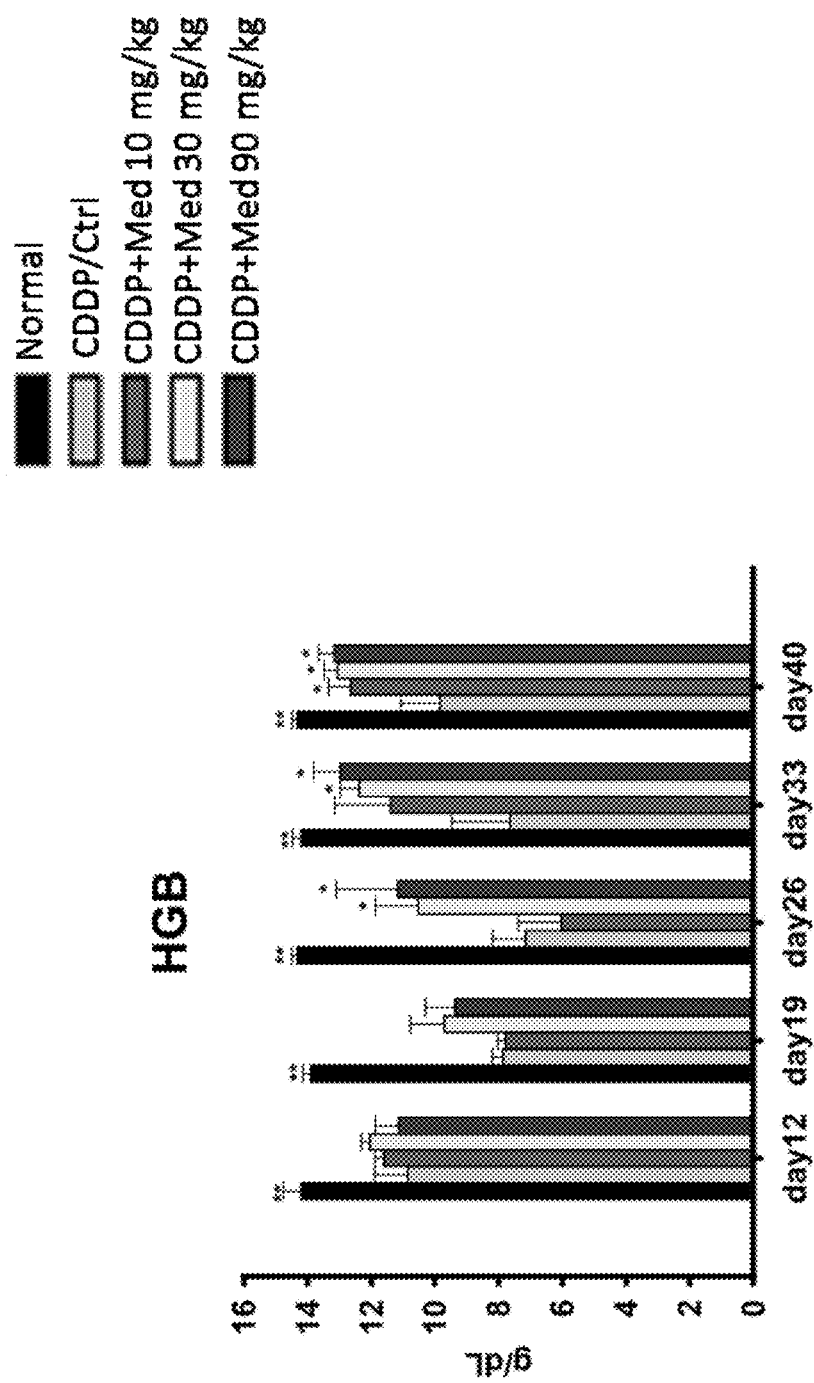
Figure 5C:
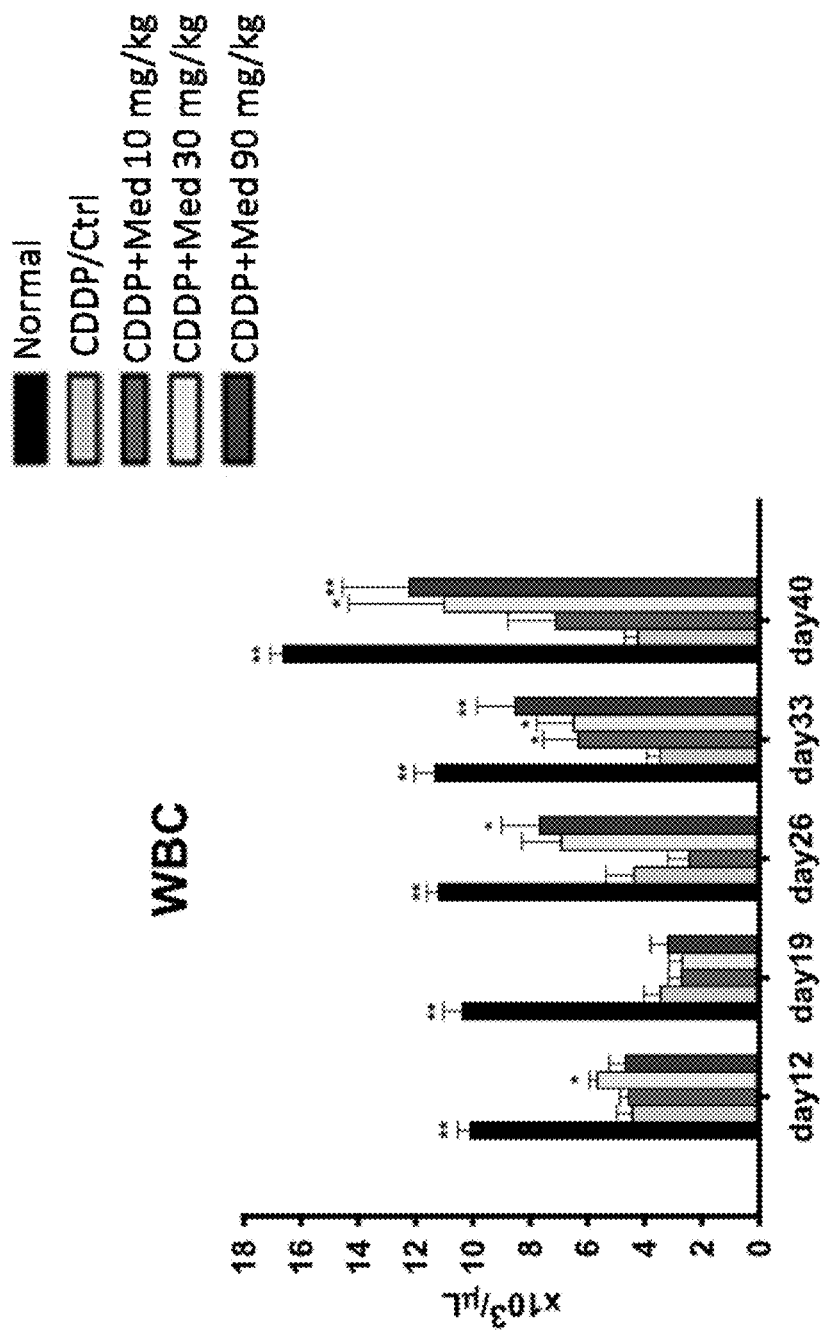
Figure 5D:
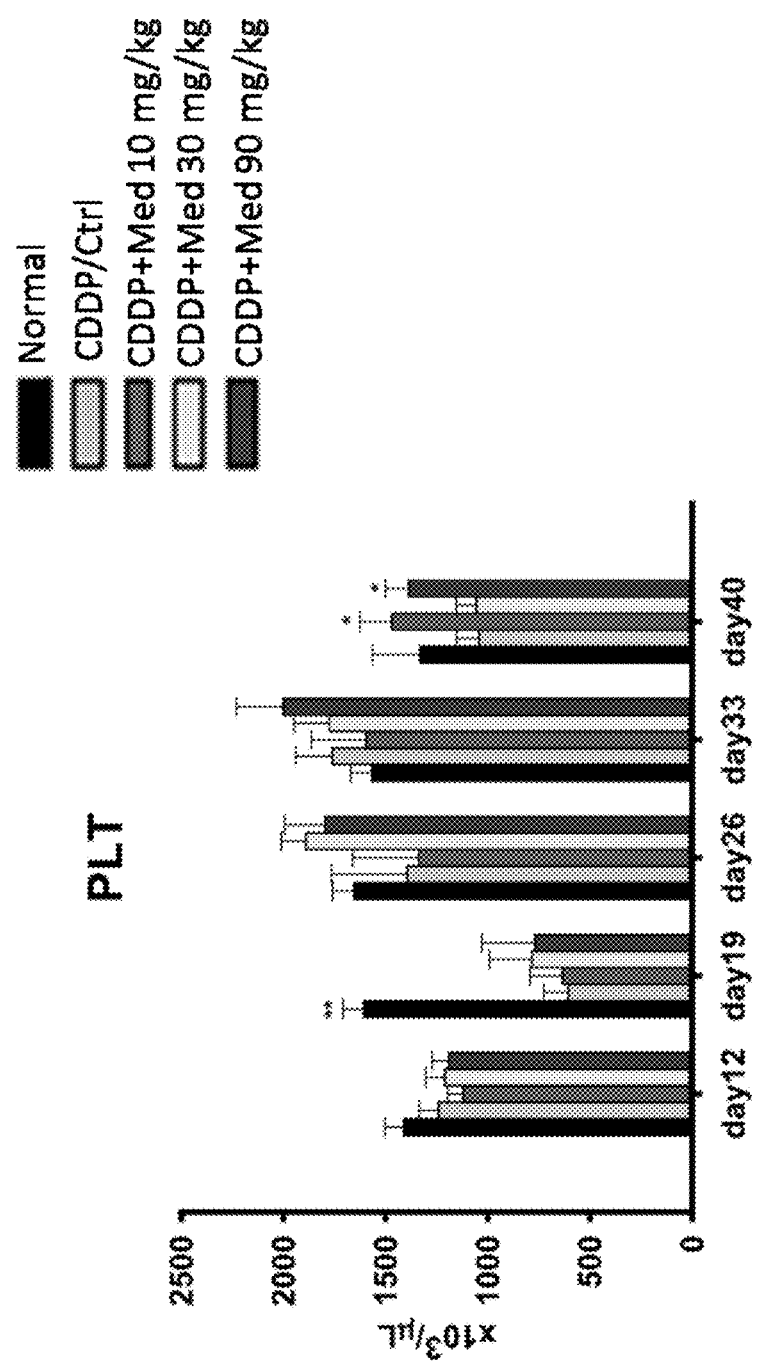
Figure 6:
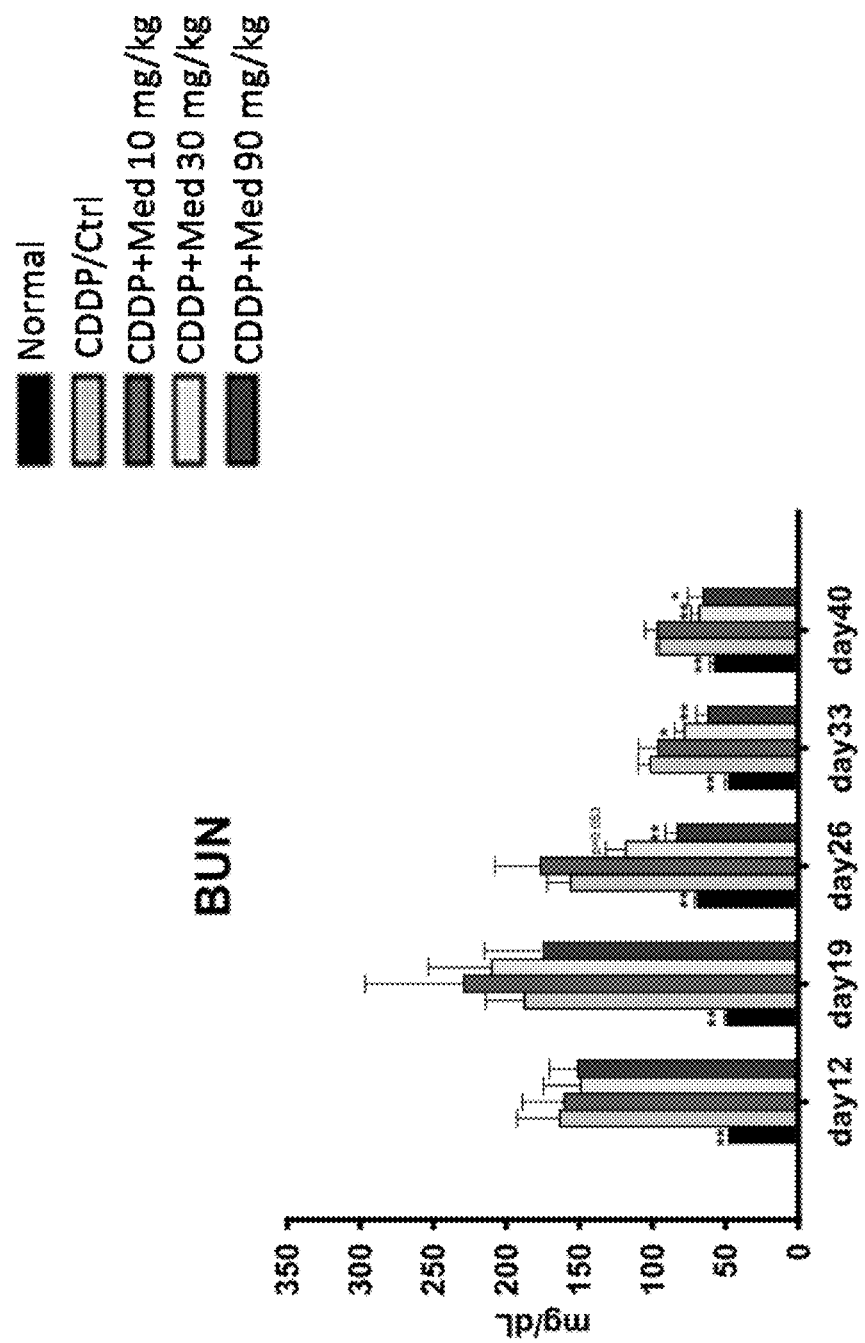
FIG. 6 is a graph showing that medicarpin accelerates the recovery from renal function in cisplatin-induced nephropathic mice.

Efficacy for (+)-Medicarpin in Animal Models a. Efficacy for Medicarpin in Cisplatin-Induced Mice Model C57BL/6J male mice (8 to 10 weeks old) were injected i.p. (Intraperitoneal) with three doses of cisplatin (CDDP) (Sigma-Aldrich), following the scheme of 7, 6 and 7 mg/kg body weight, at 1, 5, 10 day, and the normal group (n=6) was injected with saline. On day 12, serum samples were collected and assayed for blood urea nitrogen content (BUN). Mice with BUN values greater than 100 mg/100 mL were chosen for the experiment. An average 70% of injected mice were successfully induced to have renal dysfunction; the unaffected mice were excluded from the medicarpin-treating experiments. The mice were (BUN=80-300 mg/dL) subsequently divided randomly into four cohorts comprising the control and three medicarpin-treated groups, medicarpin 10, 30, 90 mg/kg/day (CDDP+Med 10, CDDP+Med 30, CDDP+Med 90) (n=6 for each group) for an additional 2 weeks. Blood samples from all the mice were collected on day 12. The red blood cell (RBC) numbers were determined from the complete blood cell count using a Sysmex Kx-21 haematology analyser (Sysmex America Inc., Mundelein, Ill., USA), and the serum BUN levels were determined through the urease GLDH method using a commercial kit (DiaSys Diagnostic System GmbH, Frankfurt, Germany). The administration and blood collection schedules were carried out according to the FIG. 4. The anaemia and impaired renal function from day 12 after the first injection of cisplatin were observed as shown in FIG. 5A and FIG. 6, and the number of red blood cell (RBC) was significantly decreased on day 19. The administration of 30 and 90 mg/kg of medicarpin on day 33 led to an almost complete recovery of anaemia. Moreover, the BUN levels of the medicarpin 30 and 90 mg/kg treatment groups were also significantly recovered. However, the number of RBC in control group without medicarpin treatment was still low. The number of RBC was recovered after high-middle dose medicarpin treatment, which indicated that the amount of hemoglobin and number of functional RBC were increased (FIG. 5B). The number of WBCs was recovered in the mice after 2 week of medicarpin treatment. Particularly, 30 and 90 mg/kg medicarpina treatments induced a significant recovery of white blood cell (WBC) during week 3 to 4 (FIG. 5C). Similarly, the number of platelet (PLT) also was decreased by cisplatin. Further, there is no significant difference between medicarpin treatment and CDDP/Ctrl group, after CDDP/Ctrl group recover from cisplatin. (FIG. 5D).

In the control group, the mice were induced to have the renal dysfunction, and the low-dose medicarpin treatment (10 mg/kg) could not improve the renal function. After 30 or 90 mg/kg of medicarpin treatment, the medicarpin accelerated the recovery from renal function in cisplatin-induced mice (FIG. 6).

Figure 7A:
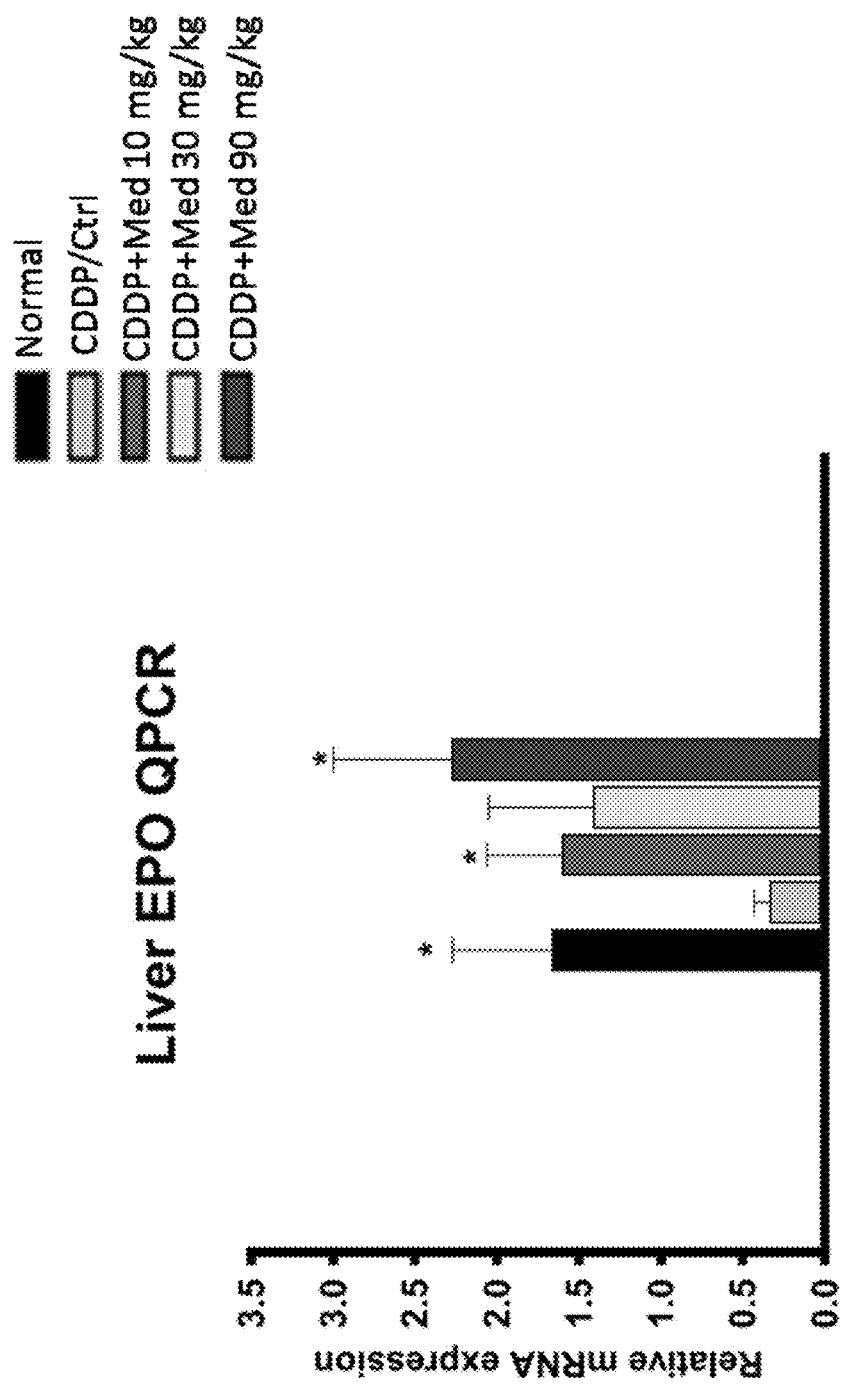
FIGS. 7A-7C are graphs showing that medicarpin enhances the expression of EPO in liver (FIG. 7A) and kidney (FIG. 7B) and the expression of HGF in liver (FIG. 7C).
Figure 7B:
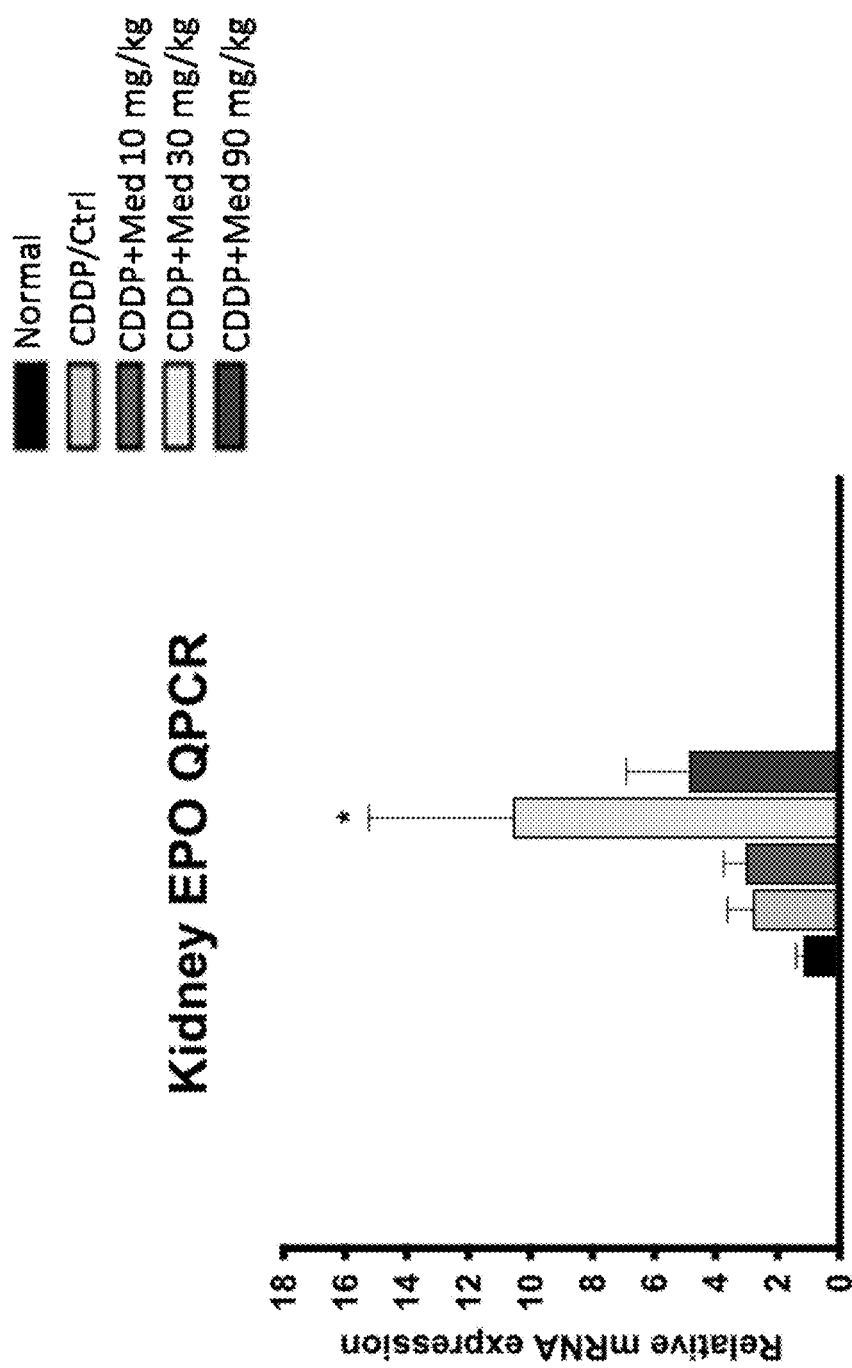
Figure 7C:
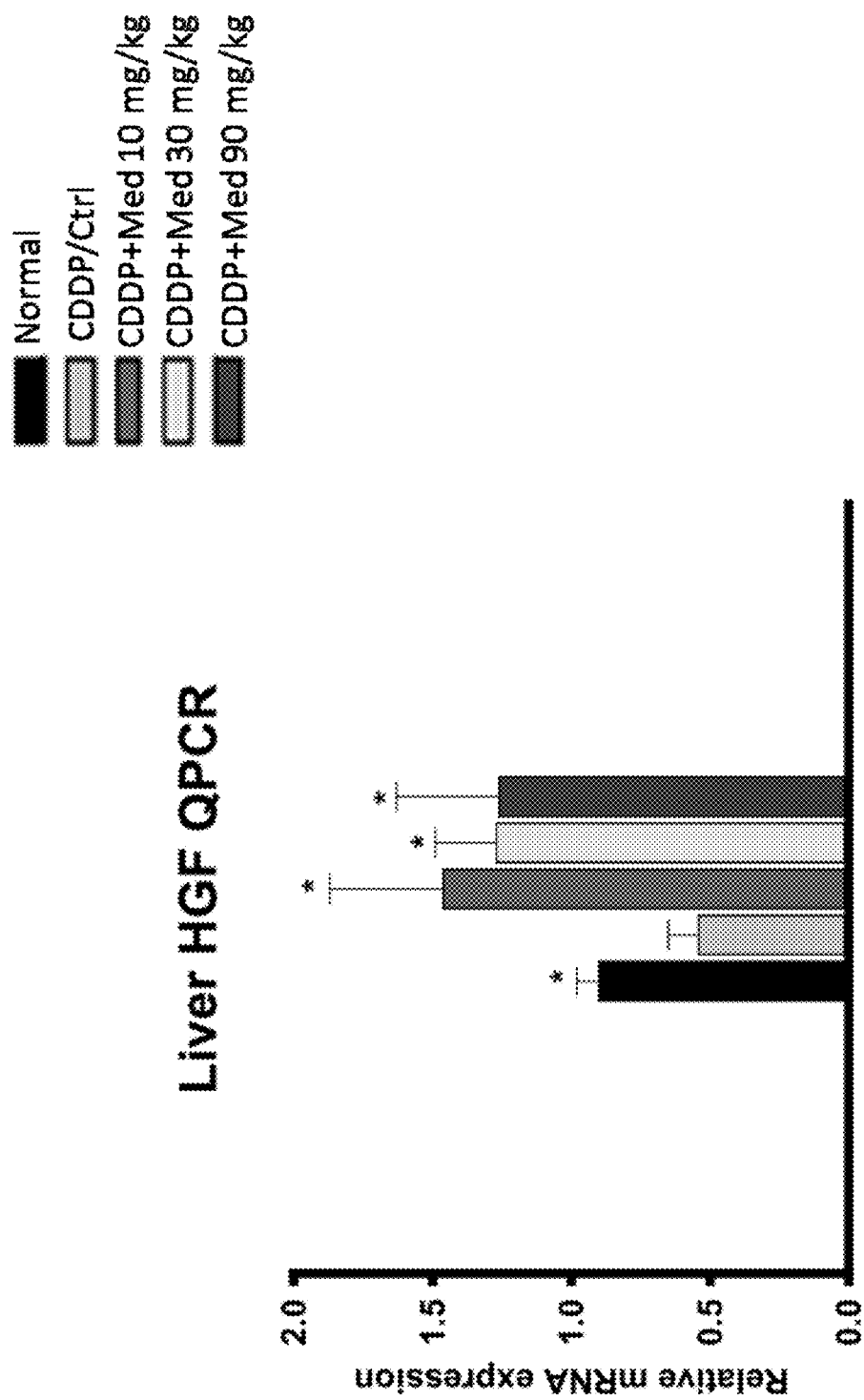
Figure 8:
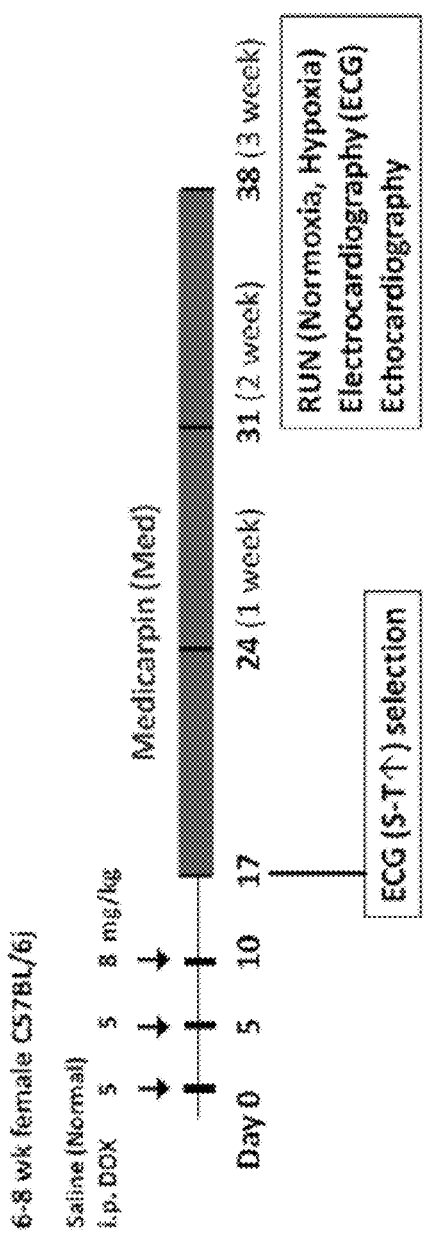
FIG. 8 is a photomicrograph of renal cortex sections stained with haematoxylin-eosin. The photomicrograph shows the regenerative effect of medicarpin on the renal cortex in cisplatin-induced nephropathic mice.

One month after treatment of medicarpin, the expression of EPO was increased in liver (FIG. 7A) and kidney (FIG. 7B) of mice. The results indicated that medicarpin could enhance the expression of EPO to impair the renal failure, and could increase the HGF expression in liver (FIG. 7C) to improve the kidney cells cell regeneration and repair (FIG. 8).

b. Efficacy for Medicarpin in Doxorubicin-Induced Mouse Model

Figure 9:
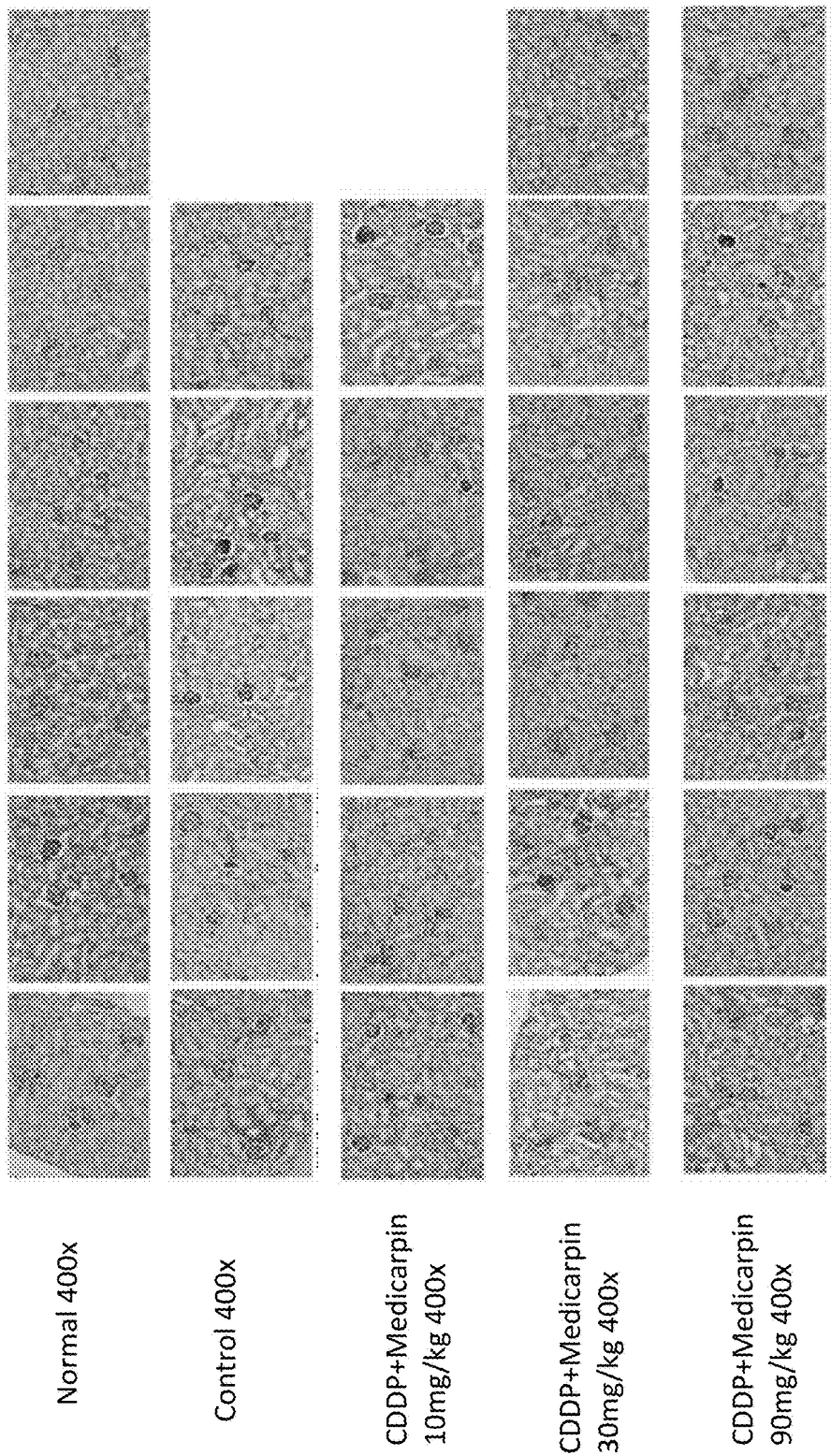
FIG. 9 is a schematic diagram showing the protocol to investigate the therapeutic effect of medicrpin in doxorubicin-induced nephropathic mice.

C57BL/6J male mice (6 to 8 weeks old) were injected intraperitoneally with triple dose of 5, 5, or 8 mg/kg doxorubicin-HCl (Sigma-Aldrich), respectively. In control group, the mice (n=6) were injected intraperitoneally with saline. 1 week after injection, the degree of heart failure was determined by the increase of S-T segment in electrocardiogram, and then the mice were randomly reclassified into the control group (Dox/Ctrl, n=9) and experimental group (Dox+Med) (FIG. 9). In the experimental group, the mice were fed a diet containing 10, 30, or 90 mg/kg/day medicarpin, respectively. Each experiment group consisted of 7 mice. After feedings, the mice were subjected to the rotarod endurance test, echocardiography and electrocardiogram. The mice were killed after an electrocardiogram and the isolated hearts were subjected to histological examination and Hb analysis. Takes 100-200 μl blood from each mice, keeps the blood in room temperature for 2 hr and centrifuged at 1200 rpm for 20 min. After centrifugation, the supernatant (serum) is for the blood biochemistry experiment.

c. Echocardiography and Electrocardiogram

The mice from all treatment groups were anaesthetized with isoflurane (0.75-1.5% inhalation); and echocardiographic measurements were taken in M-mode in triplicate for each mouse using an ATL HDI 5000 ultrasound system (Philips Medical Systems, ATL Ultrasound, Bothell, Wash., USA). The depth of anaesthesia was monitored by assessing the reaction to toe pinch and skin pinch tests and also by determining jaw tone. To assess the ECG parameters, three electrodes were utilized. The ECG tracings from lead I were recorded by means of an electrocardiograph connected to s.c. needle electrodes in the isoflurane-anaesthetized mouse. All probes were connected to an amplifier and digital converter for signal recording at the 100 mV range with low-pass 1 Hz and high-pass 1 kHz filters. An acquisition data system with LabVIEW software (National Instruments Corp., Austin, Tex., USA) was used to record and analyze the ECG signals.

Figure 10A:
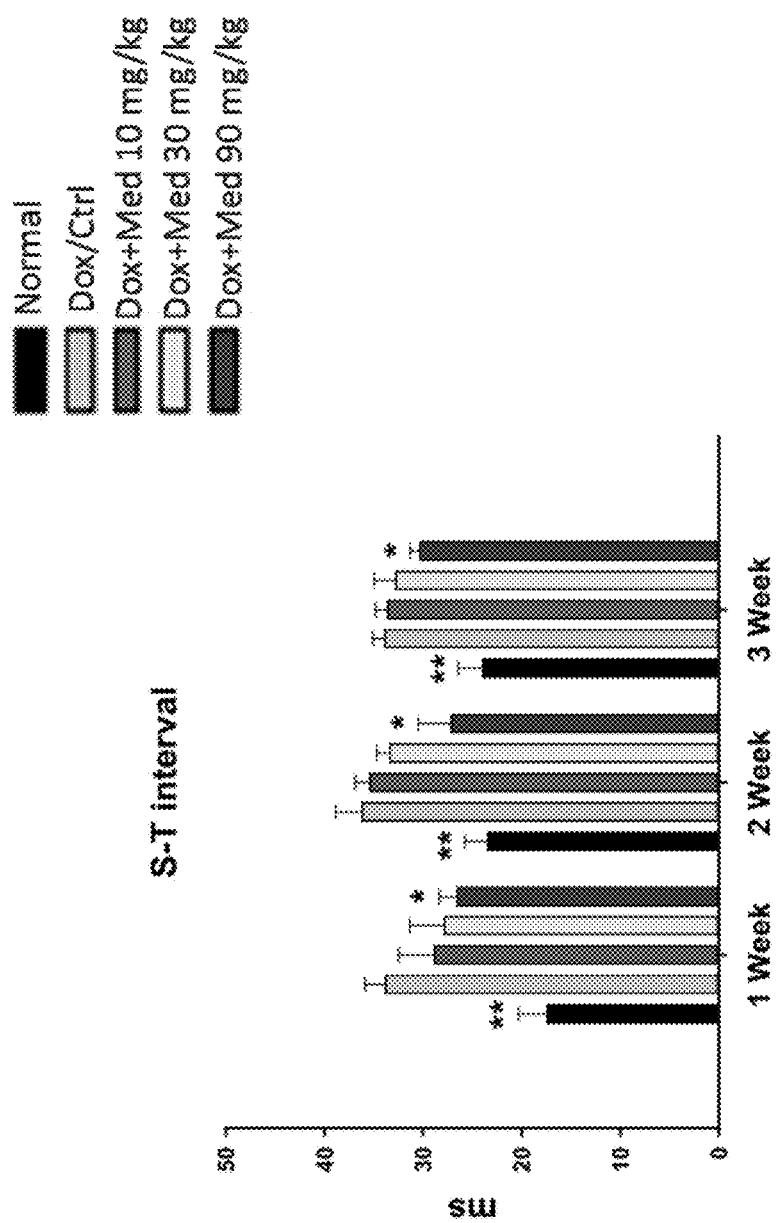
FIGS. 10A-10B are graphs showing the effect of medicarpin on cardiac function in doxorubicin-induced mice by using electrocardiography. The prolonged S-T interval was improved in the mice of experimental group (90 mg/kg/day medicarpin) as shown in FIG. 10A. Three weeks after medicarpin treatment, the heart rate (beats per second) was recovered (FIG. 10B).
Figure 10B:
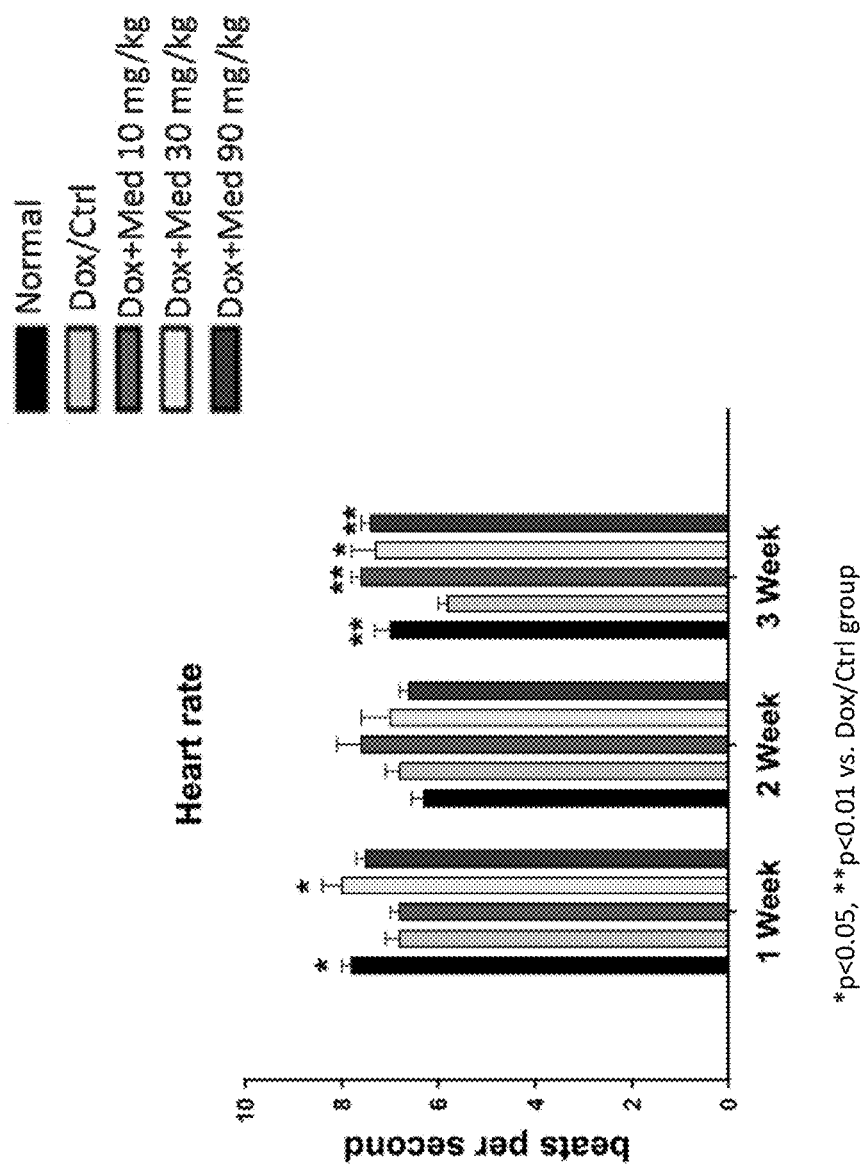
Figures 11A, 11B:
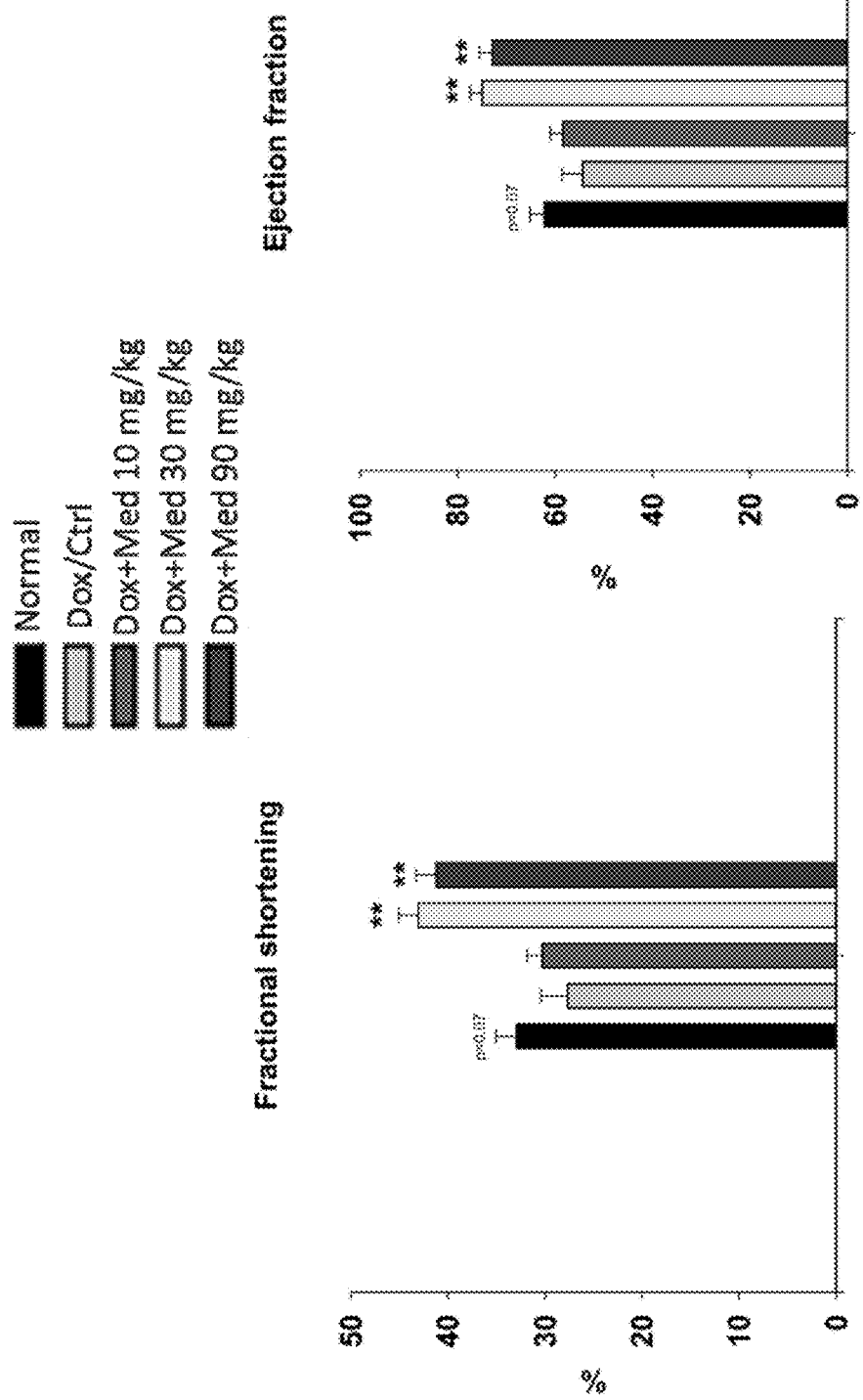
Figures 12A, 12B:
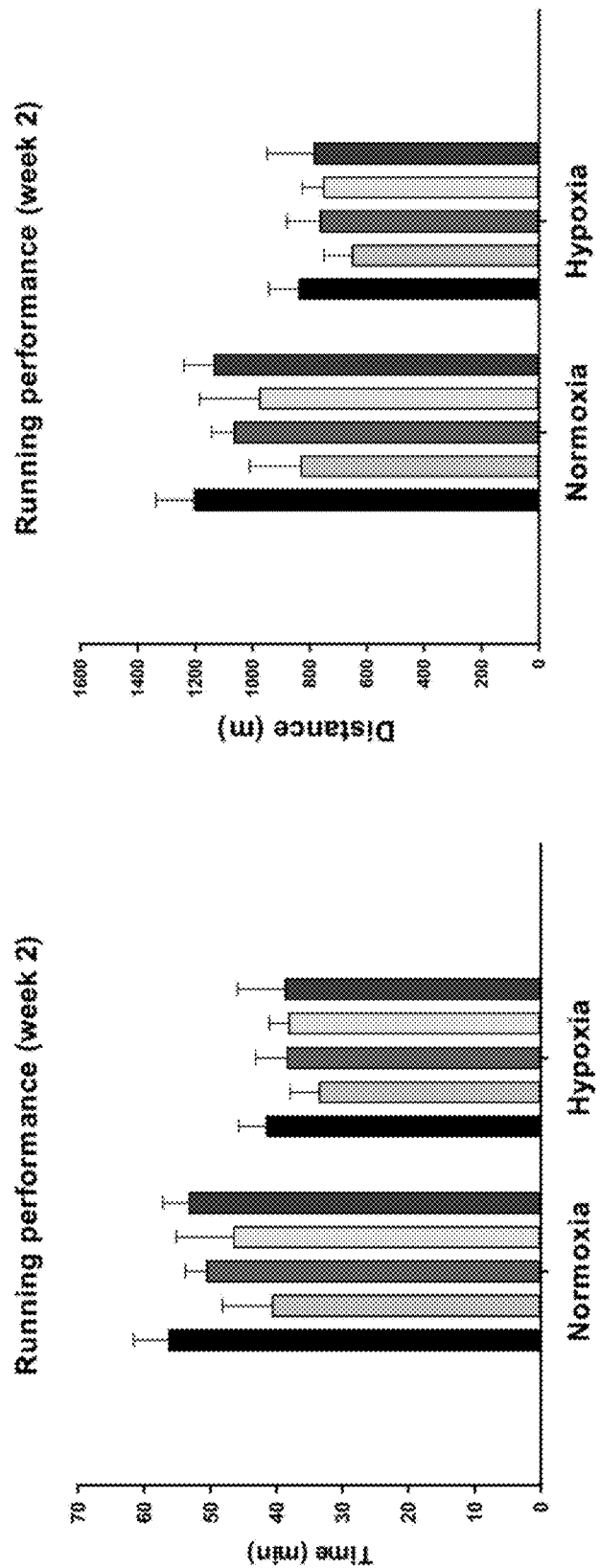
FIGS. 12A-12D are graphs showing the effect of medicarpin on the time of exhaustion (latency) and the running distance of exhaustion during the treadmill exercise under normoxic or hypoxic (8% $O_2$) conditions in doxorubicin-induced mice. The administration of medicarpin for 3 weeks enhanced the endurance performance to exhaustion under both normoxic and hypoxic conditions in a dose-dependent manner (FIGS. 12A-12D).
Figures 12C, 12D:
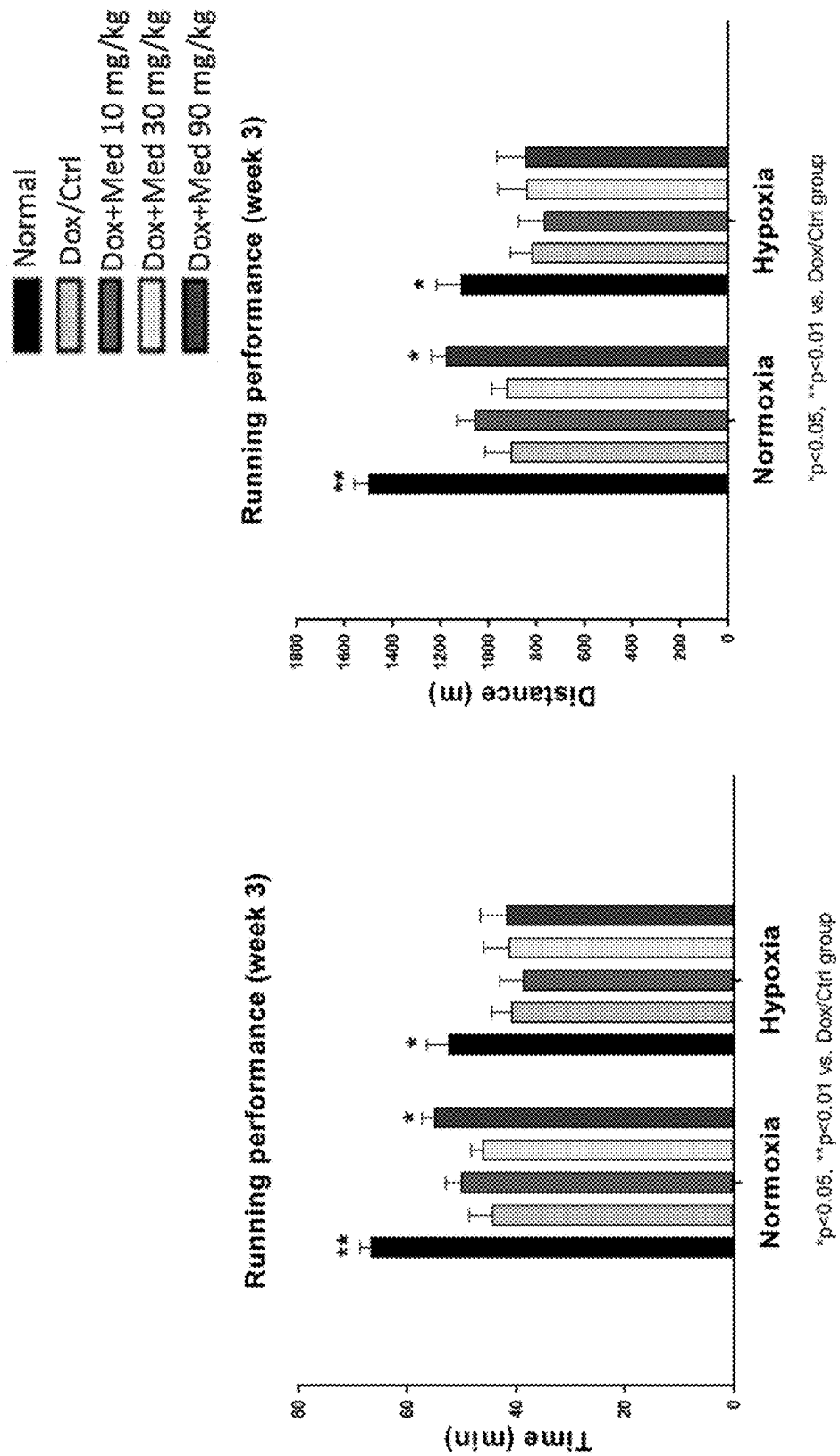
Figure 13B:
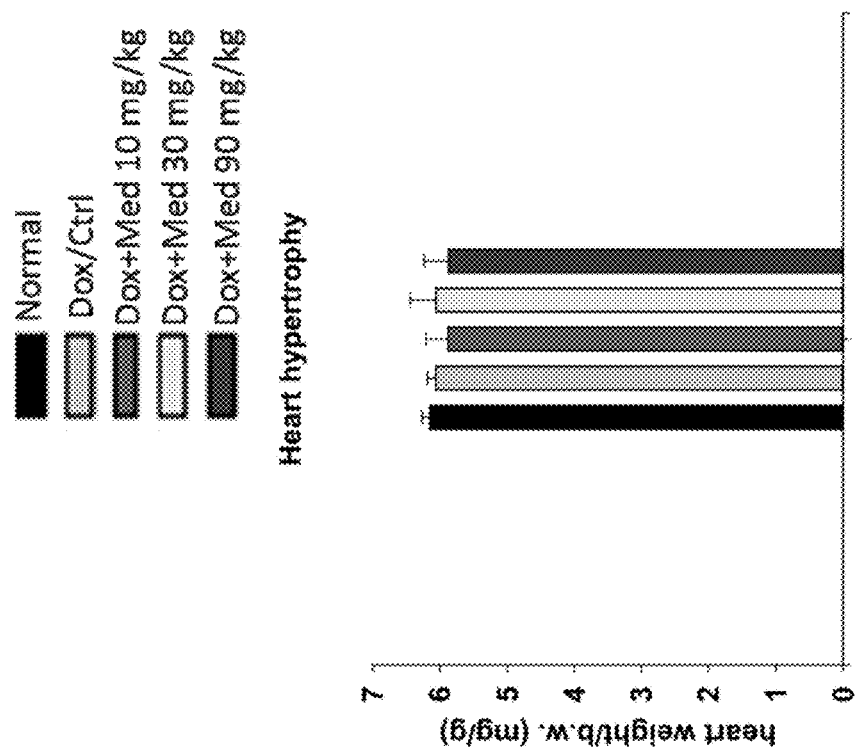
FIGS. 13A-13C are graphs showing the effect of medicarpin on the heart weight recovery and renal function in doxorubicin-induced mice. The left ventricular posterior wall thickness of mice identified by electrocardiogram was increased after medicarpin treatment, which reflected to the recovery of heart weight (FIG. 13A), and not reflected to heart hypertrophy (FIG. 13B). The medicarpin would not affect the renal function (FIG. 13C).
Figure 13A:
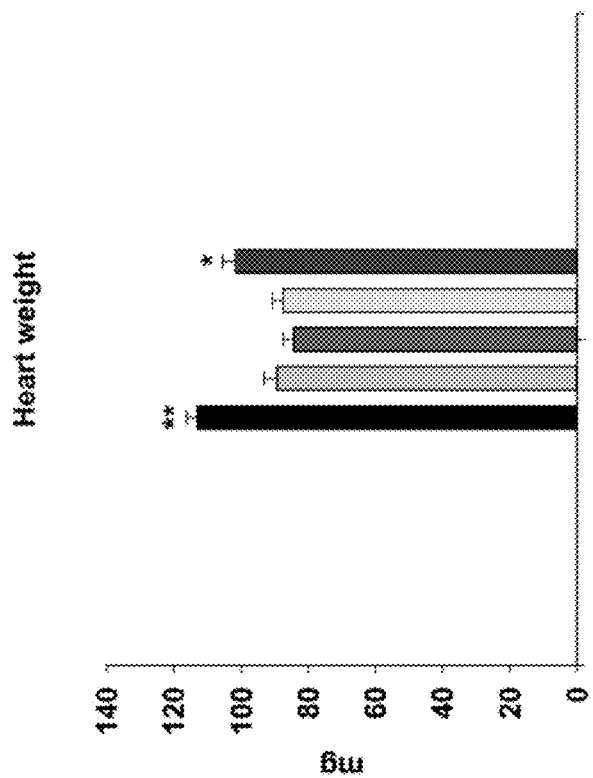
Figure 13C:
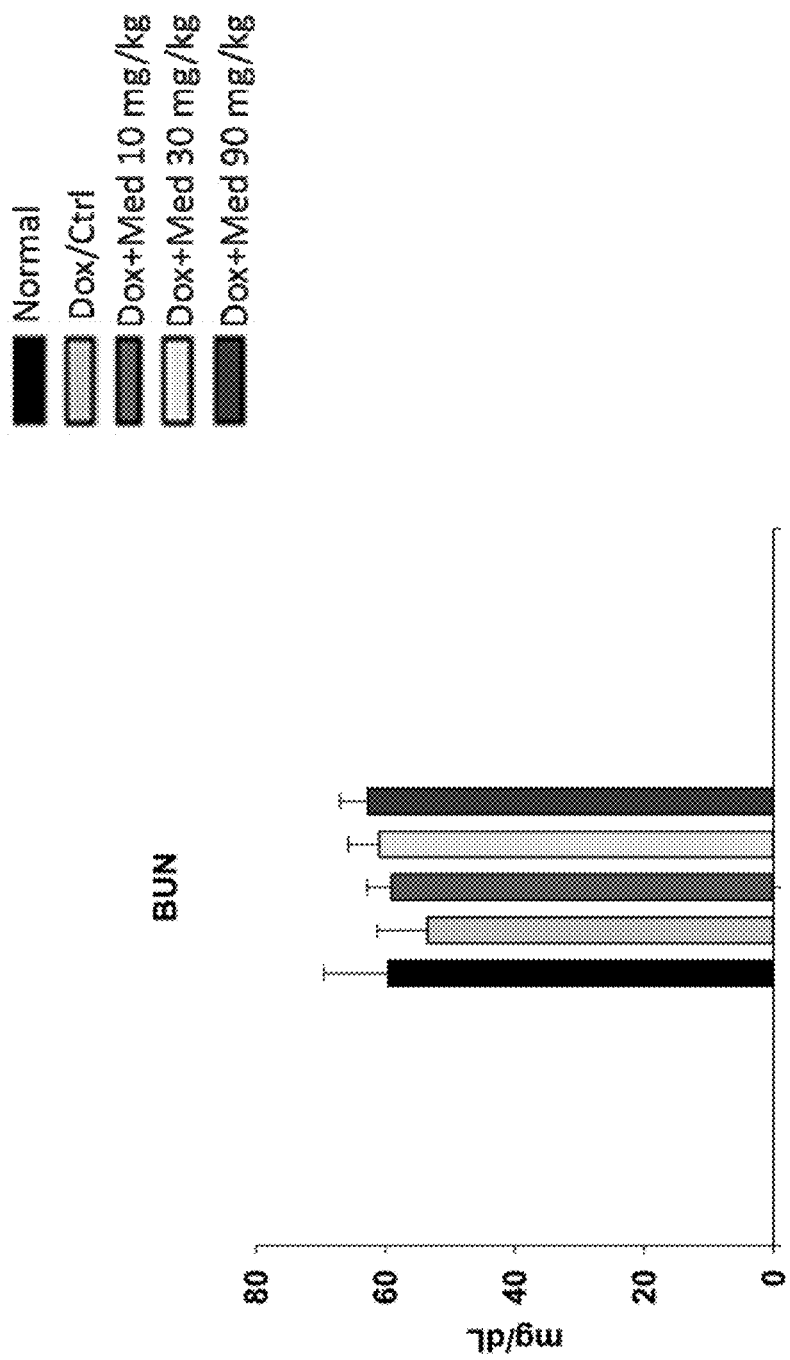

One week after medicarpin treatment, the prolonged S-T interval was still observed in the mice of the control group (Dox group), and was improved in the mice of experimental group (90 mg/kg/day medicarpin) as shown in FIG. 10A. Three weeks after medicarpin treatment, the heart rate (beats per second) was recovered to normal (FIG. 10B). Similarly, in the control group (Dox group), echocardiography performed 2 weeks after doxorubicin administration demonstrated that mice receiving doxorubicin alone had a significant deterioration in cardiac function, as characterized by decreased ejection fractions (EF) and fractional shortening (FS). By comparison, mice treated with medicarpin (30 and 90 mg/kg) had significantly greater ejection fractions and fractional shortening, shows medicarpin has the ability to recover heart function (FIGS. 11A-11D and Table 1). The left ventricular posterior wall thickness (LVPWs) of mice identified by electrocardiogram was increased after middle-high doses of medicarpin treatment, which reflected to the recovery of heart weight (FIG. 13A), and not heart hypertrophy (FIG. 13B). Besides, there is no influence to renal function (FIG. 13C).

TABLE 1

The effect of medicarpin on cardiac function is characterized by echocardiography in dox-induced cardiomyopathic mice on week 3.

|  | Normal | Dox | Dox + Med10 | Dox + Med30 | Dox + Med90 |
| --- | --- | --- | --- | --- | --- |
| IVS; d (mm) | 0.96 ± 0.03 | 0.85 ± 0.08 | 0.85 ± 0.03 | 0.81 ± 0.04 | 0.86 ± 0.05 |
| IVS; s (mm) | 1.36 ± 0.04* | 1.11 ± 0.10 | 1.20 ± 0.03 | 1.19 ± 0.02 | 1.29 ± 0.09 |
| LVID; d | 3.48 ± 0.13 | 3.38 ± 0.17 | 3.70 ± 0.34 | 3.33 ± 0.07 | 3.30 ± 0.11 |
| LVID; s | 2.34 ± 0.15 | 2.46 ± 0.20 | 2.58 ± 0.27 | 1.89 ± 0.06* | 1.94 ± 0.12* |
| LVPW; d | 0.75 ± 0.01 | 0.70 ± 0.05 | 0.69 ± 0.10 | 0.74 ± 0.04 | 0.77 ± 0.06 |
| LVPW; s | 1.02 ± 0.05 | 0.97 ± 0.06 | 1.00 ± 0.07 | 1.26 ± 0.07** | 1.15 ± 0.08* |
| FS (%) | 32.97 ± 2.12 | 27.70 ± 2.72 | 30.32 ± 1.56 | 43.04 ± 2.03** | 41.19 ± 2.07** |
| EF (%) | 62.27 ± 2.96 | 54.39 ± 4.22 | 58.44 ± 2.55 | 75.07 ± 2.29 | 72.92 ± 2.72 |

**$p < 0.01$, $p < 0.05$ vs. Dox/Ctrl group (n = 4-6)
IVS: Interventricular septum diameter; diastole (IVSd), systole (IVSs)
LVID: Left ventricular internal diameter; diastole (LVIDd), systole (LVIDs)
LVPW: Left ventricular posterior wall; diastole (LVPWd), systole (LVPWs)
FS: Fractional shortening = (LVIDd − LVIDs) × 100%/LVIDd
EF: Ejection fraction = (LVIVd − LVIVs) × 100%/LVIVd
LVIV: Left ventricular internal volume d. Rotarod Endurance Assessment

Before being divided into treatment groups, 8 to 10 week-old C57B1/6J male mice were trained on a treadmill for a maximum of 10 min for each of three consecutive training sessions per day for 3 days. After the training, the qualified mice were randomly divided into medicarpin-treating groups (10, 30 or 90 mg/kg/per day, n=5 for each group) for 7 days. On the testing day, each mouse was subjected to three trials on the treadmill at under a normoxic or hypoxic (8% $O_2$) atmosphere. The endurance performance was measured over time until the mice suffered from electric shock over 35 times/min (electric shock system is on the end of the treadmill). The maximum trial length was 60 min and there was a 30-min rest period between each trial. (Table 2)

TABLE 2

Outlines of the protocol used for the running test: the endurance performance of each mouse was measured with the treadmill exercise under normoxic or hypoxic (8% O 2) conditions.

| Week 1 | Week 2, 3 | |
| --- | --- | --- |
| Training | Habituation | Running |
| 7 m/min, 0°, 10 min | 7 m/min, 0°, 3 min | 15 m/min, 0°, 10 min |
| 10-15 m/min, 0°, 10 min | 10 m/min, 0°, 3 min | 20 m/min, 0°, 10 min |
| | 15 m/min, 0°, 5 min | 20 m/min, 5°, 20 min |
| | | 25 m/min, 5°, 20 min |
| | | 25 m/min, 10°, 20 min |
| | | 30 m/min, 10°, 20 min |

Notably, the administration of medicarpin for 3 weeks enhanced the endurance performance to exhaustion under both normoxic and hypoxic conditions in a dose-dependent manner (FIGS. 12A-12D).

e. Biochemistry Assay and Histological Examination

Figures 14A, 14B:
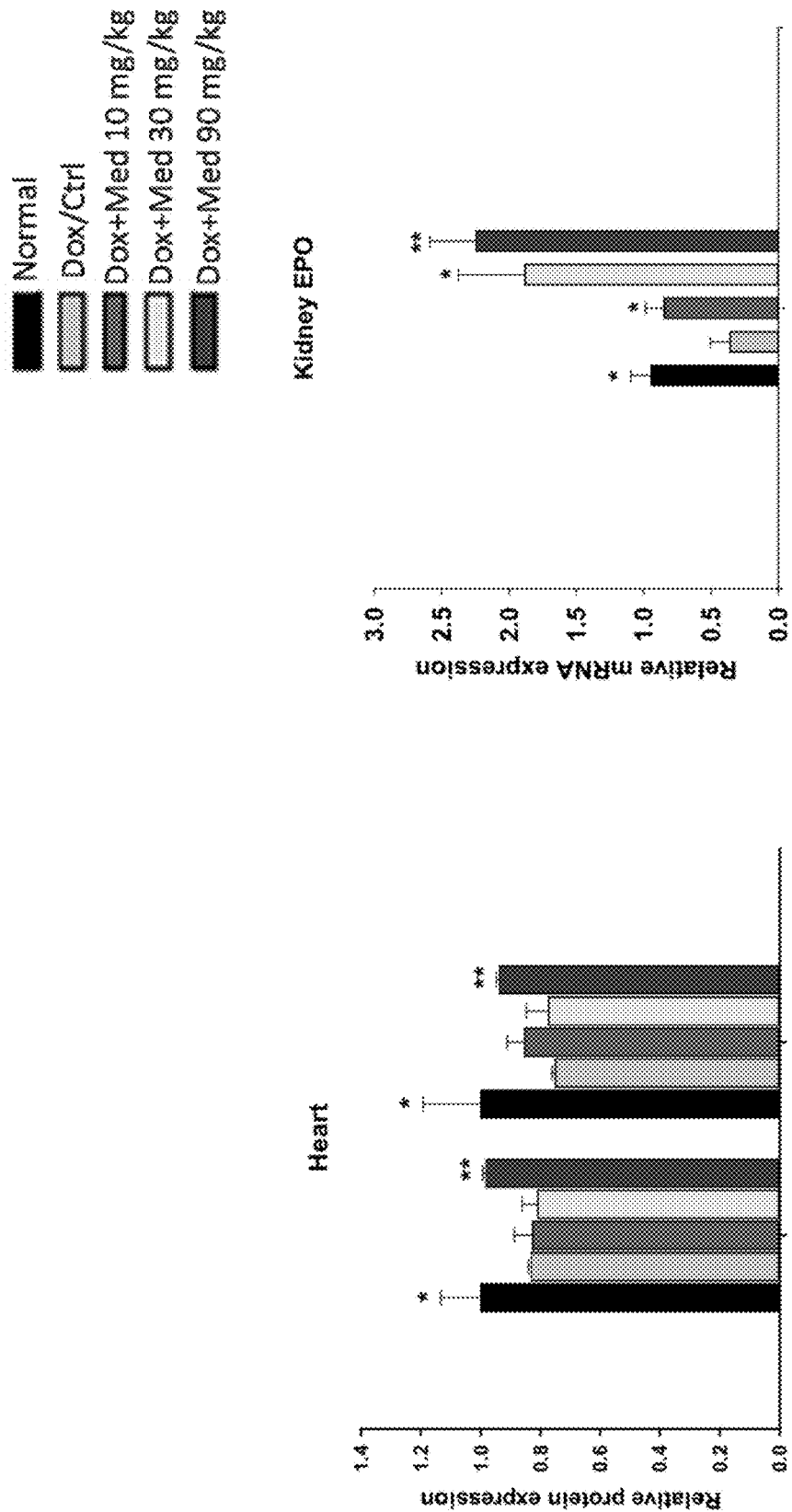
FIGS. 14A-14B are graphs showing the effect of medicarpin on the expression of PGC1 and EPO genes in heart and kidney of doxorubicin-induced mice. The expression level of EPO was recovered and increased in kidney (FIG. 14B) and heart (FIG. 14A).

The expression of EPO was recovered and increased in kidney (FIG. 14B) and heart (FIG. 14A). The results indicated that medicarpin could improve heart failure by inducing the EPO expression to markedly enhance cell repair and stimulate the mitochondrial function (PGC-1α) to increase cardiac systole.

Figure 15A:
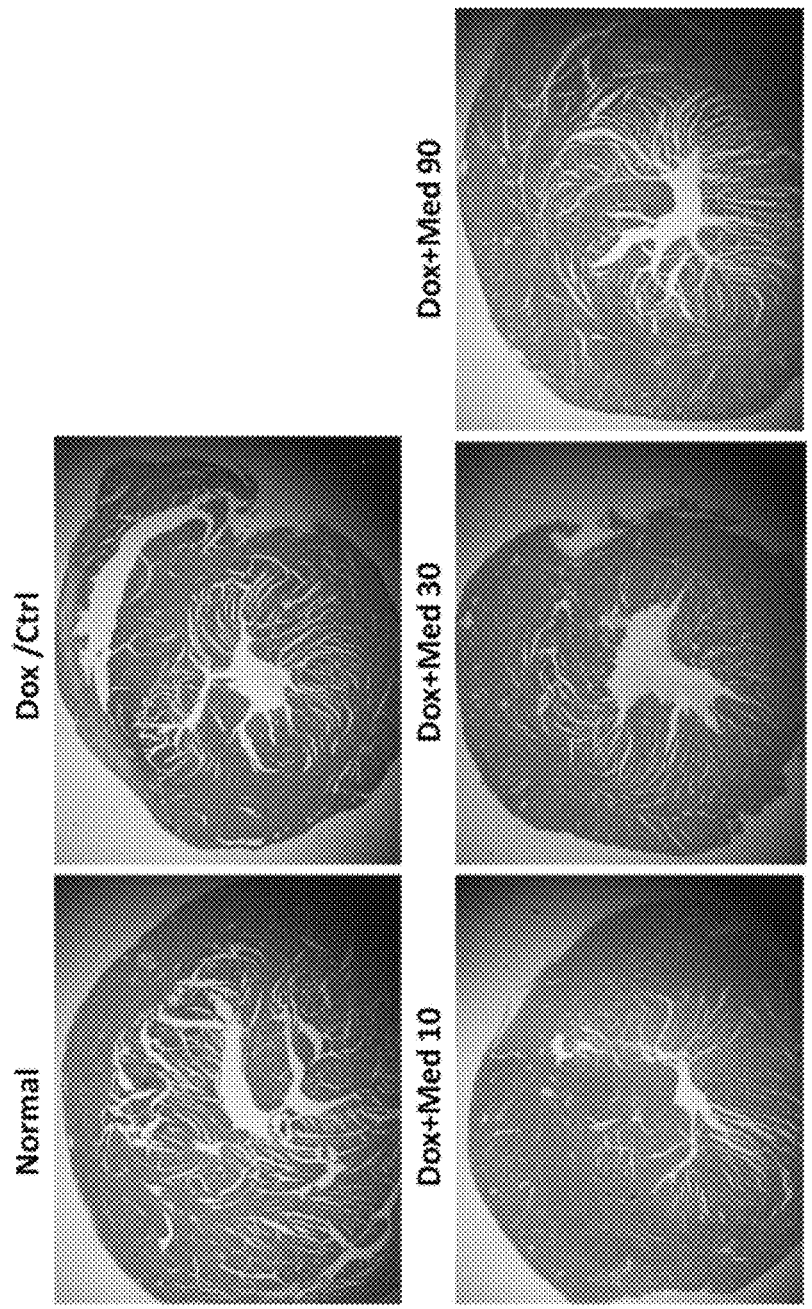
FIGS. 15A-15B are photomicrographs showing histologic evaluation of the cardiac tissues corresponding to untreated and medicarpin treated groups. The hematoxylin and eosin (H&E) stain of left ventricular sections of mouse hearts at 40× (FIG. 15A) and 400× (FIG. 15B).
Figure 15B:
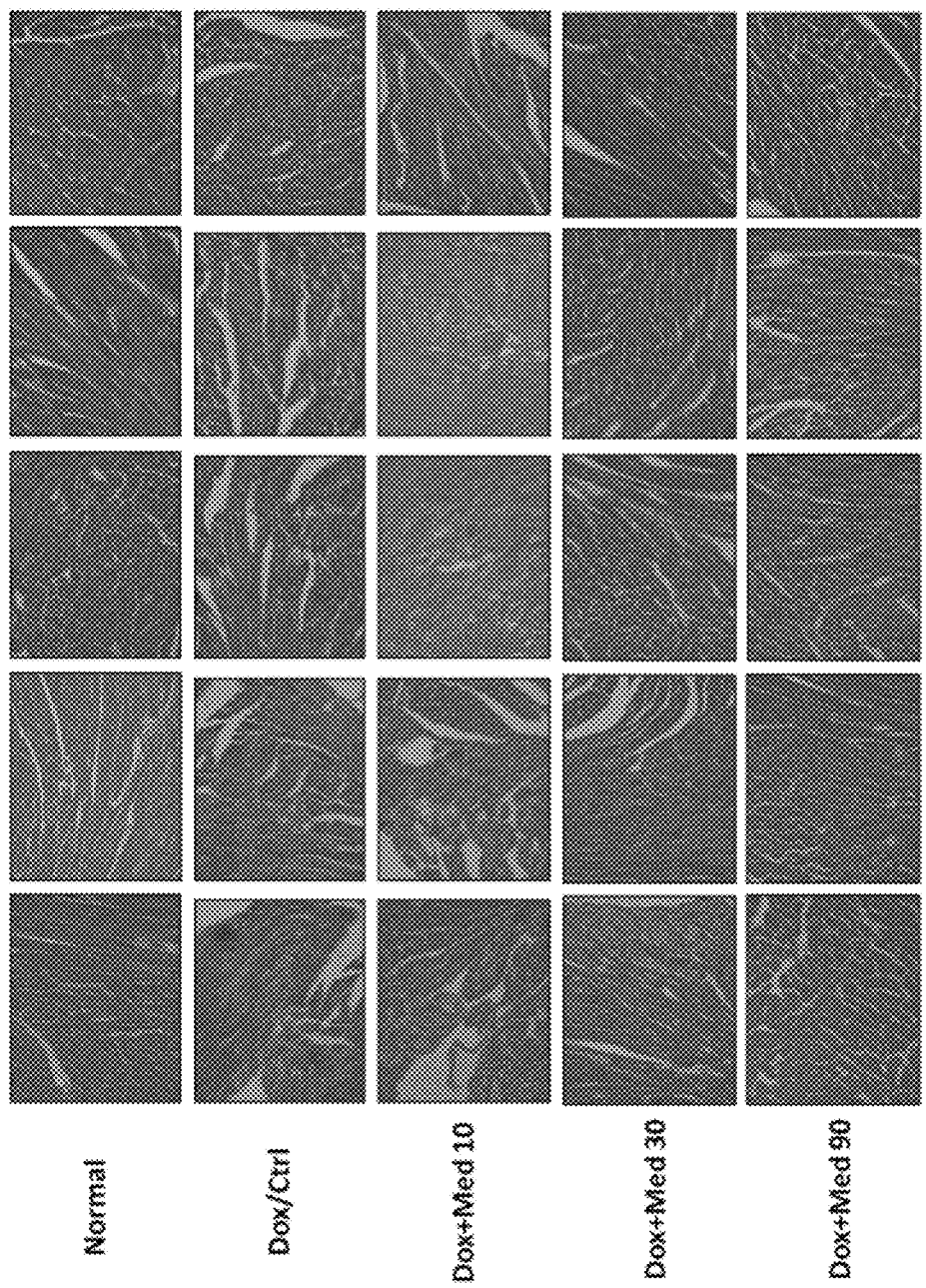
Figure 16:
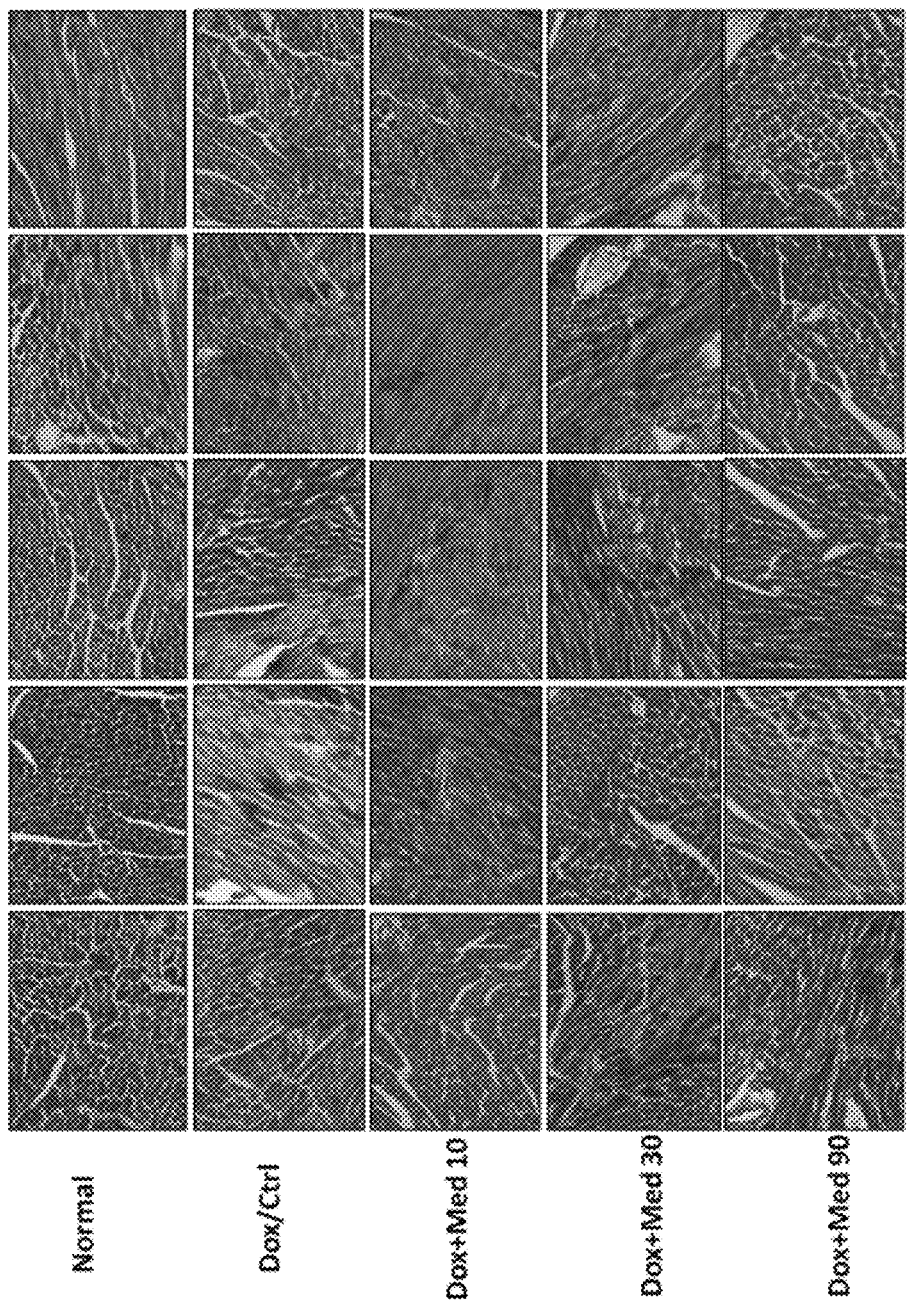
FIG. 16 is a photomicrograph showing the left ventricular sections of mice hearts stained with Masson's trichrome after medicarpin treatment on day 40 in doxorubicin-induced mice.

Referring to FIGS. 15A-15B and FIG. 16, the histochemical examination revealed the irregularity of the muscles in the ventricle walls, myocardial necrosis, cytoplasmic vacuolation, and myocardial injury in doxorubicin-induced mice. The medicarpin treatment significantly attenuated the doxorubici-induced impairment of cardiac function. Additionally, the Dox-damaged hearts presented with cardiomyocytes atrophy or hypertrophy, cytoplasmic vacuolization, myofibrillar loss and developed myocardial fibrosis and these effects were significantly ameliorated by middle-high dosed medicarpin treatment.

f. Statistics

All results described in Examples of the present invention are expressed as the mean±SEM. The statistical analysis was performed using Student's t-test. One-way ANOVA was used to examine the differences across the animal experimental groups. The post hoc differences between the means of the experimental groups were determined via Tukey's test. P<0.05 was considered significant.

Although preferred embodiments are disclosed as above, they cannot be used to limit the preset invention, and anyone skilled in the art can make some changes and modifications without exceeding the spirit and scope of the present invention, and thus the scope of the present invention will be limited only by the appended claims.

The invention claimed is:
1. A compound as shown in formula I,

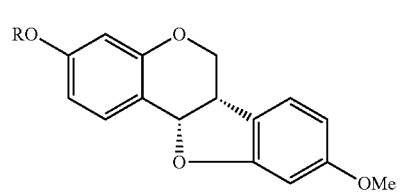

Formula I wherein R is

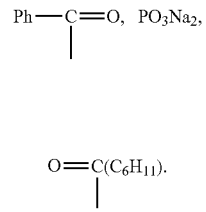

or a pharmaceutically acceptable salt thereof.

2. A method for treating organ dysfunction in a subject, wherein the method comprises administrating to said subject a pharmaceutical composition; wherein the pharmaceutical composition comprises a compound of claim 1 or a pharmaceutical acceptable salt thereof and a carrier.

3. The method for treating organ dysfunction according to claim 2, wherein the concentration of the compound is 0.1-10 μg.

4. The method for treating organ dysfunction according to claim 2, wherein the dose of the pharmaceutical composition is 30-90 mg/kg.

5. The method for treating organ dysfunction according to claim 2, wherein the compound is an inducer of erythropoietin (EPO), wherein the inducer stimulates the proliferation and differentiation of erythroid progenitor cells, and increases the number of red blood cells (RBC), white blood cells (WBC) and platelets (PLT).

6. The method for treating organ dysfunction according to claim 2, wherein the organ dysfunction is a cardiac or a renal dysfunction.

7. The method for treating organ dysfunction according to claim 6, wherein the renal dysfunction is an acute renal failure.

8. The method for treating organ dysfunction according to claim 2, wherein the pharmaceutical composition can increase the oxygen carrying capacity of red blood cells in blood, or increase the number of white blood cells (WBC).

9. The method for treating organ dysfunction according to claim 2, wherein the pharmaceutical composition can accelerate renal cortex cell regeneration.

10. The method for treating organ dysfunction according to claim 6, wherein the cardiac dysfunction is a cardiomyopathy.

11. The method for treating organ dysfunction according to claim 2, wherein the pharmaceutical composition can reduce cardiomyocytes atrophy, hypertrophy, apoptosis or myocardial fibrosis.

12. The method for treating organ dysfunction according to claim 2, wherein the pharmaceutical composition can increase endurance under normoxic condition.

* * * * *